(12) United States Patent
Lefler et al.

(10) Patent No.: US 12,188,894 B2
(45) Date of Patent: *Jan. 7, 2025

(54) ELECTROCHEMICAL FET SENSOR

(71) Applicant: QuLab Medical Ltd., Herzliya (IL)

(72) Inventors: Sharon Lefler, Herzliya (IL); Idan Tamir, Herzliya (IL); David Schreiber, Herzliya (IL); Hila Masasa, Herzliya (IL)

(73) Assignee: QuLab Medical Ltd., Herzliya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/947,891

(22) Filed: Sep. 19, 2022

(65) Prior Publication Data

US 2023/0228704 A1    Jul. 20, 2023

Related U.S. Application Data

(63) Continuation of application No. 17/514,631, filed on Oct. 29, 2021, now Pat. No. 11,448,612, which is a (Continued)

(51) Int. Cl.
*G01N 27/414* (2006.01)
*A61M 37/00* (2006.01)
*G01N 33/543* (2006.01)

(52) U.S. Cl.
CPC ....... *G01N 27/414* (2013.01); *A61M 37/0015* (2013.01); *G01N 27/4145* (2013.01); *G01N 27/4146* (2013.01); *G01N 33/5438* (2013.01)

(58) Field of Classification Search
CPC ............ G01N 27/414; G01N 27/4145; G01N 27/4146
See application file for complete search history.

(56) References Cited

U.S. PATENT DOCUMENTS 5,011,589 A * 4/1991 Amemiya ............ G01N 27/414
204/419
11,448,612 B2 * 9/2022 Lefler .................. G01N 27/414
(Continued)

FOREIGN PATENT DOCUMENTS

EP         3500168 A1    6/2019
WO    2004065952 A1    8/2004
(Continued)

OTHER PUBLICATIONS

Ginet et al., "CMOS-compatible fabrication of top-gated field-effect transistor silicon nanowire-based biosensors," J. Micromech. Microeng. 21 (2011) 065008 (7 pp) (Year: 2011).*

(Continued)

*Primary Examiner* — Alexander S Noguerola
(74) *Attorney, Agent, or Firm* — Greenberg Traurig, LLP

(57) ABSTRACT

A sensor includes a working electrode in contact with an analyte solution; an amplifier including: a source terminal; a drain terminal; a back gate terminal; and nanowires, each nanowire electrically connecting the source terminal to the drain terminal; and an insulator having a first side and a second side. The working electrode is positioned to the first side of the insulator. The source terminal, the drain terminal, and the nanowires are positioned to the second side of the insulator. The insulator prevents direct electrical contact between the working electrode, the analyte solution and either the source terminal, the drain terminal, or the nanowires. The working electrode is configured such that, when a chemical species is present in the analyte solution, a variation in an electrical field at a location of the nanowires is induced, inducing a corresponding variation in an electrical current between the source terminal and the drain terminal.

25 Claims, 15 Drawing Sheets

Related U.S. Application Data continuation of application No. PCT/IB2020/000568, filed on Jul. 10, 2020.

(60) Provisional application No. 62/873,440, filed on Jul. 12, 2019.

(56) References Cited

U.S. PATENT DOCUMENTS

| | | | | |
|---|---|---|---|---|
| 2002/0167003 | A1* | 11/2002 | Campbell | G01N 27/414 257/40 |
| 2008/0319392 | A1 | 12/2008 | Angel et al. | |
| 2011/0152654 | A1 | 6/2011 | Wang et al. | |
| 2012/0073988 | A1 | 3/2012 | Zhang et al. | |
| 2012/0143027 | A1* | 6/2012 | Phillips | G01N 27/4145 600/345 |
| 2013/0069120 | A1* | 3/2013 | Merz | G01N 27/302 257/E21.705 |
| 2014/0017772 | A1* | 1/2014 | Di Matteo | G01N 27/327 430/312 |
| 2017/0082570 | A1 | 3/2017 | Takechi et al. | |
| 2018/0106796 | A1 | 4/2018 | Sheu et al. | |
| 2018/0199873 | A1 | 7/2018 | Wang et al. | |
| 2019/0125223 | A1 | 5/2019 | Wang et al. | |

FOREIGN PATENT DOCUMENTS

| | | |
|---|---|---|
| WO | 2015059704 A1 | 4/2015 |
| WO | 2017098517 A1 | 6/2017 |
| WO | 2017098518 A1 | 6/2017 |
| WO | 2018037406 A1 | 3/2018 |
| WO | 2018037407 A1 | 3/2018 |

OTHER PUBLICATIONS

Cheol-Min Lim et al. (2017) Improved sensing characteristics of dual-gate transistor sensor using silicon nanowire arrays defined by nanoimprint lithography, Science and Technology of Advanced Materials, 18:1, 17-25, DOI: 10.1080/14686996.2016.125340 (Year: 2017).*

Anh et al., "Electroactive Gate Materials for a Hydrogen Perodixe Sensitive EMOSFET," IEEE Sensors Journal (Feb. 2002); 2(1):26-33.

Diallo et al., "Development of pH-based ElecFET biosensors for lactate ion detection," Biosensors and Bioelectronics, Elsevier (2013); 40(1):291-296.

Elfstrom et al., " Surface Charge Sensitivity of Silicon Nanowires: Size Dependence," Nano Letters (2007); 7 (9):2608-2612.

Hendrikse et al., "Characterization of the EMOSFET, a novel one-electrode chemical transducer for redox measurements," Journal of Electroanalytical Chemistry, Elsevier (1998); 458:23-29.

Hendrikse et al., "The EMOSFET as a potentiometric transducer in an oxygen sensor," Sensors and Actuators, Elsevier (1998):B47:1-8.

International Search Report for International Application No. PCT/IB2020/00568 issued Nov. 17, 2020.

Kahn et al., Gate Length Scaling of Si Nanowire FET: a NEGF Study, Conference Paper—May 2015 found at https://www.researchgate.net/publication/308829949; 4 pages.

Shen et al., Silicon nanowire field-effect-transistor based biosensors: from sensitive to ultra-sensitive, Biosensors and Bioelectronics, Elsevier (2014); 60:101-111.

Anna-Maria Pappa et al., "Organic Transistor Arrays Integrated with Finger-Powered Microfluidics for Multianalyte Saliva Testing," Advanced Healthcare Materials, p. 1-8. 2016.

Xihua Wang et al., "Silicon-based nanochannel glucose sensor," Appl. Phys. Lett, p. 1-3. 2008.

* cited by examiner

ELECTROCHEMICAL FET SENSOR

PRIORITY CLAIM

This patent application claims priority from U.S. Provisional App. No. 62/873,440, filed Jul. 12, 2019, the disclosure of which is incorporated herein by reference in its entirety.

FIELD

The present disclosure relates to sensing and, more particularly, to systems and methods for detecting biological analytes in biological liquids.

BACKGROUND

The detection of various chemical and biological analytes in aqueous or other solutions can be achieved using different established electrochemical methods, including amperometric, potentiometric or impedance-based techniques.

Many commercially available three-electrode amperometric sensors include a working electrode, a counter electrode and a reference electrode. In a typical setup, the three electrodes are in contact with, or immersed in, the analyte solution. The major dimension of a commercially available amperometric sensor, is typically around 10 mm length. In the case of amperometric techniques, a fixed voltage is applied to the reference and working electrodes, driving a redox reaction of a specific analyte and generating a detectable current between the working and counter electrodes.

Conventionally, potentiometric techniques, on the other hand, can be configured to passively measure the potential between two such electrodes, without an electrochemical reaction occurring through the passage of electrons. As such, in potentiometric measurements the analyte to be measured is not affected by the measurement process. Conventionally, potentiometric sensors minimally use a two-electrode setup including a working electrode and reference electrode to measure the change in working electrode potential caused by the presence of a redox species in solution

SUMMARY OF THE INVENTION

This summary is a high-level overview of various aspects of the invention and introduces some of the concepts that are further detailed in the Detailed Description section below. This summary is not intended to identify key or essential features of the claimed subject matter, nor is it intended to be used in isolation to determine the scope of the claimed subject matter. The subject matter should be understood by reference to the appropriate portions of the entire specification, any or all drawings, and each claim.

Embodiments of the present disclosure relate to a sensor comprising a working electrode configured to be positioned in contact with an analyte solution; an amplifier, comprising a source terminal; a drain terminal; and a plurality of nanowires, wherein each of the nanowires electrically connects the source terminal to the drain terminal; and an insulator having a first side and a second side opposite the first side, wherein the working electrode is positioned to the first side of the insulator, wherein (a) the source terminal, (b) the drain terminal, and (c) the plurality of nanowires are positioned to the second side of the insulator, whereby the insulator is configured to prevent direct electrical contact between the working electrode and either (a) the source terminal, (b) the drain terminal, or (c) the plurality of nanowires, and whereby the insulator is configured to prevent direct contact between the analyte solution and either (a) the source terminal, (b) the drain terminal, or (c) the plurality of nanowires, wherein the working electrode is configured such that, when an electron transport mediator is present in the analyte solution, a variation in an electrical field at a location of the plurality of nanowires is induced, and wherein the plurality of nanowires is configured such that, when the electrical field varies, a corresponding variation in an electrical current between the source terminal and the drain terminal is induced.

In an embodiment, the distance between the source terminal and the drain terminal is in the range of 10 microns to 100 microns.

In an embodiment, the insulator has a thickness in the range of 10 microns to 1 mm.

In an embodiment, each of the plurality of nanowires has a length in the range of 10 microns to 100 microns.

In an embodiment, the working electrode, the field-effector transistor and the insulator are in a stacked configuration.

In an embodiment, the working electrode material comprises at least one of gold, titanium or platinum.

In an embodiment, the sensor has a footprint of 0.00005 $mm^2$ to 0.005 $mm^2$.

In an embodiment, the working electrode has a major dimension of 1 micron to 10,000 microns.

In an embodiment, the nanowires have one of a square, rectangular, triangular or trapezoidal cross-section.

In an embodiment, the sensor comprises from 1 to 100 nanowires.

In an embodiment, the sensor further comprises a hydrogel disposed over the working electrode, the hydrogel including at least one enzyme configured to interact with an analyte in the analyte solution.

In an embodiment, the enzyme includes one of glucose oxidase, lactate oxidase, 3-hydroxybutyrate dehydrogenase, cholesterol oxidase, pyruvate oxidase, Glycerol oxidase, Alcohol oxidase, Glutaminase oxidase, L-glutamate oxidase, Xanthine oxidase, L-glutamate oxidase, Choline oxidase, Sarcosine oxidase and Ascorbate oxidase or Creatininase, Creatinase, Peroxidase, Laccase, Tyrosinase, Glucose dehydrogenase, Lactate dehydrogenase, Alcohol dehydrogenase or Glutamate dehydrogenase.

In an embodiment, the hydrogel is configured to interact with at least one of β-d-Glucose, L-lactate, Glutamine, cholesterol, Glycerol, pyruvate, Ethanol L-glutamate, Choline Acetylcholine, I-Ascorbic acid, cortisol, Creatine, Creatinine, 2-hydroxybutyrate, 3-hydroxybutyrate or Acetoacetate.

In an embodiment, the electron transport mediator is one of hydrogen peroxide, nicotinamide adenine dinucleotide (NADH), ascorbic acid, caffeine, acetaminophen, flavin adenine dinucleotide (FAD) and flavin mononucleotide (FMN) or quinone cofactors.

In an embodiment, the sensor further comprises an adhesive layer deposited on the working electrode, the adhesive layer configured to adhere the hydrogel to the working electrode.

In an embodiment, each of the nanowires has a diameter in the range of 1 to 500 nanometers.

Embodiments of the present disclosure also relate to a microprobe sensing device, comprising: a plurality of microprobes, each microprobe including a tip configured to be inserted into an analyte solution and a sensor positioned at the tip, each sensor comprising: a working electrode configured to be positioned in contact with the analyte solution;

an amplifier comprising: a source terminal; a drain terminal; and a plurality of nanowires, wherein each of the nanowires electrically connects the source terminal to the drain terminal, wherein each of the nanowires has a diameter in the range of 1 to 500 nanometers; and an insulator having a first side and a second side opposite the first side, wherein the working electrode is positioned to the first side of the insulator, wherein (a) the source terminal, (b) the drain terminal, and (c) the plurality of nanowires is positioned to the second side of the insulator, whereby the insulator is configured to prevent direct electrical contact between the working electrode and either (a) the source terminal, (b) the drain terminal, or (c) the plurality of nanowires, and whereby the insulator is configured to prevent direct contact between the analyte solution and either (a) the source terminal, (b) the drain terminal, or (c) the plurality of nanowires, wherein the working electrode is configured such that, when an electron transport mediator is present in the analyte solution, a variation in an electrical field at a location of the plurality of nanowires is induced, and wherein the plurality of nanowires is configured such that, when the electrical field varies, a corresponding variation in an electrical current between the source terminal and the drain terminal is induced.

In an embodiment, each sensor on the plurality of microprobes shares the working electrode.

In an embodiment, the plurality of microprobes is configured to detect at least two electron transport mediators.

In an embodiment, the plurality of microprobes is positioned in parallel.

Embodiments of the present disclosure also relate to a method of determining the presence of glucose in an analyte solution, the method comprising: inserting a tip of a first microprobe and a tip of a second microprobe of a sensing device into the analyte solution, each of the first and second microprobes including a sensor positioned at the tip, each sensor comprising: a working electrode configured to be positioned in contact with an analyte solution; an amplifier, comprising: a source terminal; a drain terminal; and a plurality of nanowires, wherein each of the nanowires electrically connects the source terminal to the drain terminal; and an insulator having a first side and a second side opposite the first side, wherein the working electrode is positioned to the first side of the insulator, wherein (a) the source terminal, (b) the drain terminal, and (c) the plurality of nanowires is positioned to the second side of the insulator, whereby the insulator is configured to prevent direct electrical contact between the working electrode and either (a) the source terminal, (b) the drain terminal, or (c) the plurality of nanowires, and whereby the insulator is configured to prevent direct contact between the analyte solution and either (a) the source terminal, (b) the drain terminal, or (c) the plurality of nanowires, wherein the working electrode of the sensor of the first microprobe includes a hydrogel embedded therein, the hydrogel containing glucose oxidase; inducing a first variation in a first electrical field at a location of the plurality of nanowires of the sensor of the first microprobe by (a) reaction of the glucose oxidase with the glucose in the analyte solution to form hydrogen peroxide and (b) redox reactions of the working electrode of the sensor of the first microprobe with (1) redox species present in the analyte solution, and (2) the hydrogen peroxide formed by the reaction of the glucose oxidase with the glucose; inducing a second variation in a second electrical field at a location of the plurality of nanowires of the sensor of the second microprobe by redox reactions of the working electrode of the sensor of the second microprobe with the redox species present in the analyte solution; inducing a first variation in a first electrical current between the source terminal of the sensor of the first microprobe and the drain terminal of the sensor of the first microprobe, the first variation in the first electrical current corresponding to the first variation of the first electrical field; inducing a second variation in a second electrical current between the source terminal of the sensor of the second microprobe and the drain terminal of the sensor of the second microprobe, the second variation in the second electrical current corresponding to the second variation of the second electrical field; and determining an amount of glucose present in the analyte solution based on a difference between the first variation in the first electrical current and the second variation in the second electrical current.

Embodiments of the present disclosure also relate to a method for electrochemically filtering the undesired detection of interfering chemical species present in an analyte solution, the method comprising: inserting a sensor positioned at a tip of a sensing device into an analyte solution, the sensor comprising: a working electrode configured to be positioned in contact with an analyte solution; an amplifier, comprising: a source terminal; a drain terminal; and a plurality of nanowires, wherein each of the plurality of nanowires electrically connects the source terminal to the drain terminal; and an insulator having a first side and a second side opposite the first side, wherein the working electrode is positioned to the first side of the insulator, wherein (a) the source terminal, (b) the drain terminal, and (c) the plurality of nanowires are positioned to the second side of the insulator, whereby the insulator is configured to prevent direct electrical contact between the working electrode and either (a) the source terminal, (b) the drain terminal, or (c) the plurality of nanowires, and whereby the insulator is configured to prevent direct contact between the analyte solution and either (a) the source terminal, (b) the drain terminal, or (c) the plurality of nanowires, wherein the working electrode is configured such that, when an chemical species are present in the analyte solution, a variation in an electrical field at a location of the plurality of nanowires is induced, wherein the plurality of nanowires is configured such that, when the electrical field varies, a corresponding variation in an electrical current between the source terminal and the drain terminal is induced, adjusting (a) a backgate voltage; (b) a working electrode voltage; and (c) a source voltage such that the minimum variation in an electrical current between the source terminal and the drain terminal is induced by the presence of an undesired chemical species.

Embodiments of the present disclosure also relate to a method for calibrating sensitivity and drift correction, the method comprising: inserting a sensor positioned at a tip of a sensing device into an analyte solution, the sensor comprising: a working electrode configured to be positioned in contact with an analyte solution; an amplifier, comprising: a source terminal; a drain terminal; and a plurality of nanowires, wherein each of the plurality of nanowires electrically connects the source terminal to the drain terminal; and an insulator having a first side and a second side opposite the first side, wherein the working electrode is positioned to the first side of the insulator, wherein (a) the source terminal, (b) the drain terminal, and (c) the plurality of nanowires are positioned to the second side of the insulator, whereby the insulator is configured to prevent direct electrical contact between the working electrode and either (a) the source terminal, (b) the drain terminal, or (c) the plurality of nanowires, and whereby the insulator is configured to prevent direct contact between the analyte solution and either (a) the source terminal, (b) the drain terminal, or (c) the plurality of nanowires, wherein the working electrode is configured such that, when an chemical species are present in the analyte solution, a variation in an electrical field at a location of the plurality of nanowires is induced, wherein the plurality of nanowires is configured such that, when the electrical field varies, a corresponding variation in an electrical current between the source terminal and the drain terminal is induced, identifying a singularity point in the performance graph of a sensor for a given analyte by adjusting (a) a backgate voltage (b) a working electrode voltage and (c) a source voltage, such that a maximum variation in an electrical current between the source terminal and the drain terminal is induced by the presence of the analyte.

BRIEF DESCRIPTION OF THE DRAWINGS

Some embodiments of the present disclosure are herein described, by way of example only, with reference to the accompanying drawings. With specific reference now to the drawings in detail, particulars shown are by way of example and for purposes of illustrative discussion of the embodiments of the invention. In this regard, the description taken with the drawings makes apparent to those skilled in the art how embodiments of the invention may be practiced.

DETAILED DESCRIPTION

Figure 1:
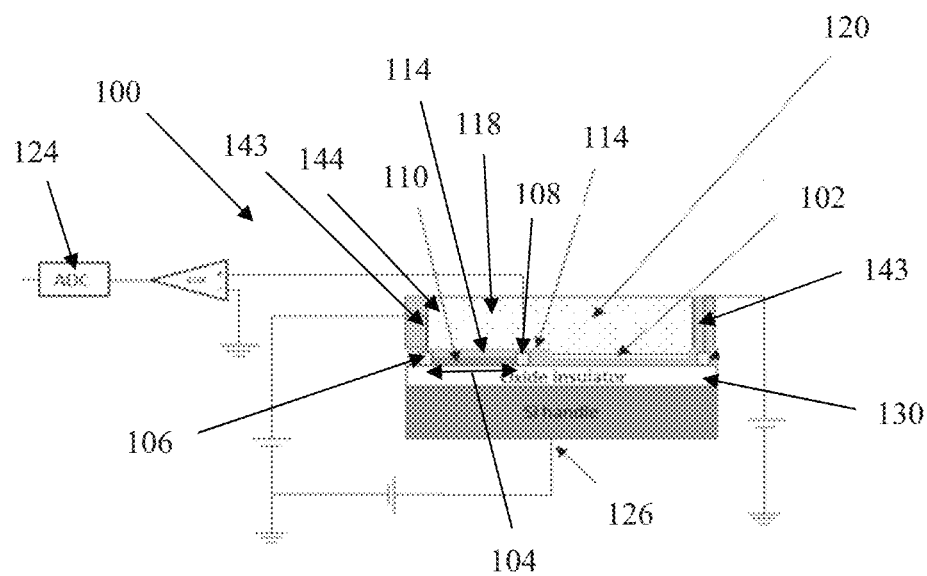
FIG. 1 is a schematic illustration of an exemplary silicon nanowire (SiNW) field-effect transistor (FET) sensor according to some embodiments of the present disclosure.

The following description of the preferred embodiment(s) is merely exemplary in nature and is in no way intended to limit the invention, its application, or uses. As used throughout, ranges are used as shorthand for describing each and every value that is within the range. Any value within the range can be selected as the terminus of the range. In addition, all references cited herein are hereby incorporated by referenced in their entireties. In the event of a conflict between a definition in the present disclosure and that of a cited reference, the present disclosure prevails.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention.

Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such.

Terms such as "attached," "affixed," "connected," "coupled," "interconnected," "mounted" and similar refer to a relationship wherein structures are secured or attached to one another either directly or indirectly through intervening structures, as well as both movable or rigid attachments or relationships, unless expressly described otherwise.

As used in the specification and the claims, the singular form of "a", "an", and "the" include plural referents unless the context clearly dictates otherwise.

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

The terms "first", "second", and the like are not intended to refer to any particular order or chronology, but instead refer to different conditions, properties, or elements.

All documents referred to herein are "incorporated by reference" in their entirety.

The term "at least" means "greater than or equal to". The term "not greater than" means "less than or equal to".

The term "includes" is synonymous with "comprises".

As used herein, the term "BGM" refers to blood glucose monitoring.

As used herein, the term "CGM" refers to continuous glucose monitoring.

As used herein, the term "working electrode" or "WE", is also referred to as the "front gate electrode" or as a "water gate electrode". The working electrode is typically a metal, e.g. gold, deposited electrode, connected to a voltage source.

As used herein, the term "working electrode voltage" or "WE voltage" is the electrical potential applied to the WE by a voltage source meter/potentiometer.

As used herein, the term "work function" or "WF" describes the energy needed to remove an electron from a solid to a point in the vacuum outside the solid surface. The WF presents the electrical potential, which is manifested at the surface/interface of, e.g. the surface/interface potential at the WE situated in a solution. The WF is measured in electron volts, eV.

As used herein, the term "Isd" or "source-drain current" refers to the electrical current which is passing through a semiconductor transistor from its source electrode to its drain electrode.

As used herein, the term "back gate" or "Bg" refers to the more remote (relative to the WE or front gate) electrical biasing voltage gate which in most cases is positioned at the bottom part (handle) of a silicon SOI (Silicon On Insulator) wafer. In biological as well as electrochemical applications, the FETs Bg is electrically separated from the solution/analyte.

As used herein, the term "trans-conductance graph" refers to the electrical characteristic that relates the current-through-the-output of a device to the voltage-across-the-input of a device. The trans-conductance values are obtained by measuring the lsd while continuously changing (sweeping) the front/back gate potential.

As used herein, the term "threshold voltage" or "Vth" of a field-effect transistor (FET) refers to the minimum gate-to-drain voltage that is needed to create a conducting path between the source and drain terminals.

As used herein, the term "wire" refers to any material having conductivity, namely having an ability to pass charge through itself, on itself and/or within its bulk. In some embodiments, a hollow structure, defined as a nanotube may be used.

As used herein, the term "nanowire" refers to a type of nanoscale, elongated semiconductor wire-like structure, most often formed from a silicon precursor by etching of a solid or through catalyzed growth from a vapor or liquid phase. For example, in some embodiments, the nanowire may be a "silicon nanowire" or "SiNW".

As used herein, the term "PB" refers to a phosphate buffer.

As used herein, the term "glucose oxidase" or "GOX" refers to an enzyme which is an oxido-reductase that catalyzes the oxidation of glucose to hydrogen peroxide and D-glucono-δ-lactone.

As used herein, the term "lactate oxidase" or "LOX" refers to a FMN (Flavin mononucleotide)-dependent alpha hydroxyl acid oxidizing enzyme. The enzyme catalyzes the oxidation of L-lactate to pyruvate in the presence of dissolved oxygen, forming hydrogen peroxide.

As used herein, the term "interstitial fluid" or "tissue fluid" or "ISF" refers to the solution that bathes and surrounds the cells of multicellular animals. The interstitial fluid is found in the interstitial spaces, also known as the tissue spaces.

As used herein, the term "field-effect transistor" or "FET" refers to an electronic device which uses an electric field to control the flow of current. This is achieved by the application of a voltage to the gate terminal, which in turn alters the conductivity between the drain and source terminals. FETs are also known as unipolar transistors since they involve single-carrier-type operation. Many different types of field effect transistors exist. Field effect transistors generally display very high input impedance at low frequencies.

As used herein, the term "metal-oxide-semiconductor field-effect transistor" or "MOSFET" refers to a type of field-effect transistor, most commonly fabricated by the controlled oxidation of silicon. It has an insulated gate, whose voltage determines the conductivity of the device.

As used herein, the term "complementary metal oxide semiconductor field-effect transistor" or "CMOS-FET" refers to a typical design style using complementary and symmetrical pairs of p-type and n-type MOSFETs.

As used herein, the term "ion-sensitive field-effect transistor" or "ISFET" refers to a field-effect transistor used for measuring ion concentrations in solution; when the ion concentration (such as H+, see pH scale) changes, the current through the transistor will change accordingly. Here, the solution is used as the gate electrode. A voltage between substrate and oxide surfaces arises due to an ion sheath.

As used herein, the term "electrochemical detection" refers to an analytical method that can detect electric currents or the change in electrical potential generated from redox reactions or interaction in test compounds.

As used herein, the term "oxidation reduction reaction" or "redox reaction" refers to a type of chemical reaction that involves a transfer of electrons between two species. Oxidation refers to the loss of electrons or an increase in oxidation state by a molecule, atom, or ion and "reduction" refers to the gain of electrons or a decrease in oxidation state by a molecule, atom, or ion.

As used herein, the term "amperometry" or "voltammetry", when used in chemical applications, refers to detection of chemical species in a solution based on electric current or changes in electric current. For example, amperometry is used in electrophysiology to study vesicle release events using a carbon fiber electrode.

As used herein, the term "potentiometry", when used in chemical applications, refers to detection of chemical species in a solution based on the changes in the electrical potential.

As used herein, the term "amperometric titration" refers to a type of titration in which the determination of the equivalence point is done by measuring the electric current produced by the titration reaction. Amperometry can be used for the estimation of equivalence point and end point in titration.

As used herein, the term "potentiometric titration" is a technique similar to direct titration of a redox reaction. It is a useful means of characterizing an acid. No indicator is required; instead the potential is measured across the analyte, typically an electrolyte solution.

As used herein, the term "nonspecific sensor" or "calibration microneedle" describes a FET sensor with or without hydrogel layer which contain no enzyme or analyte-specific membrane. The purpose of such sensor is to detect the background (basal level) of a chemical species in an analyte. This nonspecific sensor is used to substructure the environment changes in the tissue such as intrinsic redox and temperature effect from the actual specific measurement which is recorded be a different sensor.

As used herein, the phrase "Chemical species" describes atoms, molecules, molecular fragments, ions, etc., being subjected to a chemical process or to a measurement. Generally, a chemical species can be defined as an ensemble of chemically identical molecular entities that can explore the same set of molecular energy levels on a defined time scale.

As used herein, the phrase "redox reactive species" describes a moiety or a compound that can participate in a redox reaction or reduction-oxidation reactions, either as an oxidizer or a reductant, and is capable of altering an oxidation number of one or more atoms of another substance. This phrase is used to describe both an oxidizer and a reductant.

As used herein, an "oxidizer", which is also referred to interchangeably as "an oxidizing/oxidative agent" or "an oxidizing/oxidative moiety" or "an oxidizing/oxidative species" describes a moiety, species or a compound that is capable of elevating the oxidation number of one or more atoms of another substance. Typically, such an alteration involves transformation of protons from the other substance to the oxidizing moiety or compound. Exemplary oxidizing agents that are suitable for being detected using a sensing system as described include, but are not limited to, reactive oxygen species (ROS) or compounds generated by reactive oxygen species.

A reactive oxygen species includes oxygen-containing molecules and/or ions in which an oxygen atom is in a free radical form (having an unpaired electron) or molecules or ions that readily generate species featuring one or oxygen free radical or oxygen in singlet state. Examples include, without limitations: ozone, peroxides, RO—, and ROO—, in which R is an organic moiety or hydrogen. In the presence of water or any other protic solvent, ROS typically generate hydrogen peroxide. Hydrogen peroxide or any other peroxide is therefore an exemplary oxidizing agent according to some embodiments of the present invention.

As used herein, a "reductant" is also referred to interchangeably as "a reducing reductive agent" or "a reducing/reductive moiety" or "a reducing/reductive species", and describes a moiety, species or a compound that is capable of reducing the oxidation number of another substance. Typically, such an alteration involves transformation of protons from the reducing agent to the other substance.

Reducing agents include, for example, moieties or species that upon release of one or more protons form a stable anion. Exemplary such agents include, for example, hydroxyl-containing agents that form a stable enolate anion upon releasing one or more protons. Compounds or moiety containing an amine-oxide group are given herein as an example. N-alkyl- or N,N-dialkyl-hydroxyl amines (e.g., DMHA) are given as a representative example. Any other known reducing agents are also contemplated.

As used herein, "debye length" describes the distance over which significant charge separation can occur.

As used herein, the term "hydrogel" describes a three-dimensional fibrous network containing at least 20%, typically at least 50%, or at least 80%, and up to about 99.99% (by mass) water. A hydrogel can be regarded as a material which is mostly water, yet behaves like a solid or semi-solid due to a three-dimensional crosslinked solid-like network, made of natural and/or synthetic polymeric chains, within the liquid dispersing medium. According to some embodiments of the present invention, a hydrogel may contain polymeric chains of various lengths and chemical compositions, depending on the precursors used for preparing it. The polymeric chains can be made of monomers, oligomers, block-polymeric units, which are inter-connected (cross-linked) by chemical bonds (covalent, hydrogen and ionic/complex/metallic bonds, typically covalent bonds). The network-forming material comprises either small aggregating molecules, particles, or polymers that form extended elongated structures with interconnections (the crosslinks) between the segments. The crosslinks can be in the form of covalent bonds, coordinative, electrostatic, hydrophobic, or dipole-dipole interactions or chain entanglements between the network segments. In the context of the present embodiments, the polymeric chains are preferably hydrophilic in nature.

The hydrogel, according to embodiments of the present invention, can be of biological origin or synthetically prepared.

According to some embodiments of the present invention, the hydrogel is biocompatible, and is such that when a biological moiety is impregnated or accumulated therein, an activity is the biological moiety is maintained, that is, a change in an activity of the biological moiety is no more than 30%, or no more than 20%, or no more than 10%, compared to an activity of the biological moiety in a physiological medium. The biological moiety can be sensing moiety or analyte.

Exemplary polymers or co-polymers usable for forming hydrogel according to the present embodiments include polyacrylates, polymethacrylates, polyacrylamides, polymethacrylamides, polyvinylpyrrolidone and copolymers of any of the foregoing. Other examples include polyethers, polyurethanes, and poly(ethylene glycol), functionalized by cross-linking groups or usable in combination with compatible cross linking agents.

Some specific, non-limiting examples, include: poly(2-vinylpiridine), poly(acrylic acid), poly(methacrylic acid), poly(N-isopropylacrylamide), poly(N,N'-methylenbisacrylamide), poly(N—(N-propyl)acrylamide), poly(methacyclic acid), poly(2-hydroxyacrylamide), poly(ethylene glycol) acrylate, poly(ethylene glycol)methacrylate, and polysaccharides such as dextran, alginate, agarose, and the like, and any copolymer of the foregoing.

In some embodiments, hydrogel precursors forming such polymeric chains are contemplated, including any combination thereof.

Hydrogels are typically formed of, or are formed in the presence of, di- or tri- or multi-functional monomers, oligomer or polymers, which are collectively referred to as hydrogel precursors or hydrogel-forming agents, having two, three or more polymerizable groups. The presence of more than one polymerizable group renders such precursors crosslinkable, and allow the formation of the three-dimensional network.

Exemplary crosslinkable monomers include, without limitation, the family of di- and triacrylates monomers, which have two or three polymerizable functionalities, one of which can be regarded as a crosslinkable functional group. Exemplary diacrylates monomers include, without limitation, methylene diacrylate, and the family of polyethylene glycol)n dimethacrylate (nEGDMA). Exemplary triacrylates monomers include, without limitation, trimethylolpropane triacrylate, pentaerythritol triacrylate, tris (2-hydroxy ethyl) isocyanurate triacrylate, isocyanuric acid tris(2-acryloyloxyethyl) ester, ethoxylated trimethylolpropane triacrylate, pentaerythrityl triacrylate and glycerol triacrylate, phosphinylidynetris(oxyethylene) triacrylate.

Hydrogels may take a physical form that ranges from soft, brittle and weak to hard, elastic and tough material. Soft hydrogels may be characterized by rheological parameters including elastic and viscoelastic parameters, while hard hydrogels are suitably characterized by tensile strength parameters, elastic, storage and loss moduli, as these terms are known in the art.

The softness/hardness of a hydrogel is governed inter glia by the chemical composition of the polymer chains, the "degree of crosslinking" (number of interconnected links between the chains), the aqueous media content and composition, and temperature.

A hydrogel, according to some embodiments of the present invention, may contain macromolecular polymeric and/or fibrous elements which are not chemically connected to the main crosslinked network but are rather mechanically intertwined therewith and/or immersed therein. Such macromolecular fibrous elements can be woven (as in, for example, a mesh structure), or non-woven, and can, in some embodiments, serve as reinforcing materials of the hydrogel's fibrous network. Non-limiting examples of such macromolecules include polycaprolactone, gelatin, gelatin methacrylate, alginate, alginate methacrylate, chitosan, chitosan methacrylate, glycol chitosan, glycol chitosan methacrylate, hyaluronic acid (HA), HA methacrylate, and other non-crosslinked natural or synthetic polymeric chains and the likes. According to some of any of the embodiment of the present invention, the amount of such non-crosslinked additives is small and typically does not exceed 100 mg in 1 ml of the hydrogel-forming precursor solution.

In some embodiments, the hydrogel is porous and in some embodiments, at least a portion of the pores in the hydrogel are nanopores, having an average volume at the nanoscale range.

In some of any of the embodiments described herein, the hydrogel is covalently attached to the nanostructure's surface by means of covalent bonds formed between the hydrogel and compatible reactive groups on the surface of the nanostructures, directly or via a linker.

As used herein, the term "analyte" is also referred to interchangeably as "target analyte" or "target molecule", and encompasses chemical and biological species, including small molecules and biomolecules such as, but not limited to, peptides, proteins, nucleotides, oligonucleotides, and polynucleotides.

In some embodiments, the sample is a biological sample, as described herein, and the analyte is a bioanalyte, that is, a chemical or biological species that is present in biological systems, for example, a biological system of a subject, as defined herein.

In some embodiments the term analyte can refer to explosives, narcotics, as well as other hazardous materials.

In some embodiments, the bioanalyte is a biomarker.

As used herein, the term "biomarker" describes a chemical or biological species which is indicative of a presence and/or severity of a disease or disorder in a subject. Exemplary biomarkers include small molecules such as metabolites, and biomolecules such as antigens, hormones, receptors, and any other proteins, as well as polynucleotides. Any other species indicative of a presence and/or severity of medical conditions are contemplated.

As used herein, the term "affinity moiety" refers to a molecule which binds with a predetermined affinity and preferably specificity to the marker or biomarker.

As used herein, the term "amine-oxide" describes a —N(OR')(R") or a —N(OR')— group, where R' and R" are as defined herein. This term refers to a —N(OR')(R") group in cases where the amine-oxide is an end group, as this phrase is defined hereinabove, and to a —N(OR')"— group in cases where the amine-oxide is an end group, as this phrase is defined hereinabove.

Whenever a group, moiety or compound as described herein is substituted, the substituent can be, for example, one or more of hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine, as defined herein.

As used herein, the term "ligand" means an ion or molecule (functional group) that binds to a central metal atom to form a coordination complex. The bonding with the metal generally involves formal donation of one or more of the ligand's electron pairs.

As used herein, the term "peroxides" describes a group of compounds with the structure R—O—O—R.[1] The O—O group in a peroxide is called the peroxide group or peroxo group. In contrast to oxide ions, the oxygen atoms in the peroxide ion have an oxidation state of −1.

As used herein, the term "calomel" describes a mercury chloride mineral with formula Hg2Cl2. Calomel is used as the interface between metallic mercury and a chloride solution in a saturated calomel electrode, which is used in electrochemistry to measure pH and electrical potentials in solutions, In most electrochemical measurements, it is necessary to keep one of the electrodes in an electrochemical cell at a constant potential. This so-called reference electrode allows control of the potential of a working electrode.

As used herein, the term "Pt electrode" describes a Platinum electrode used because it can easily adsorb hydrogen as well as being inert metal does not participates in redox reaction during working of cell.

As used herein, the term "halide" and "halo" describes fluorine, chlorine, bromine or iodine.

As used herein, the term "haloalkyl" describes an alkyl group as defined above, further substituted by one or more halide.

As used herein, the term "sulfate" describes a —O—S(=O)2-OR' end group, as this term is defined hereinabove, or an —O—S(=O)2-O— linking group, as these phrases are defined hereinabove, where R' is as defined hereinabove.

As used herein, the term "thiosulfate" describes a —O—S(=S)(=O)—OR' end group or a —O—S(=S)(=O)—O— linking group, as these phrases are defined hereinabove, where R' is as defined hereinabove.

As used herein, the term "sulfite" describes an —O—S(=O)—O—R' end group or a group linking group, as these phrases are defined hereinabove, where R' is as defined hereinabove.

As used herein, the term "thiosulfite" describes a —O—S(=S)—OR' end group or an —O—S(=S)—O— group linking group, as these phrases are defined hereinabove, where R' is as defined hereinabove.

As used herein, the term "sulfinate" describes a —S(=O)—OR' end group or an —S(=O)—O— group linking group, as these phrases are defined hereinabove, where R' is as defined hereinabove.

As used herein, the term "sulfoxide" or "sulfinyl" describes a —S(=O)R' end group or an —S(=O)— linking group, as these phrases are defined hereinabove, where R' is as defined hereinabove.

As used herein, the term "sulfonate" describes a —S(=O)2-R' end group or an —S(=O)2- linking group, as these phrases are defined hereinabove, where R' is as defined herein.

As used herein, the term "S-sulfonamide" describes a —S(=O)2-NR'R" end group or a —S(=O)2-NR'— linking group, as these phrases are defined hereinabove, with R' and R" as defined herein.

As used herein, the term "N-sulfonamide" describes an R'S(=O)2-NR"— end group or a —S(=O)2-NR'— linking group, as these phrases are defined hereinabove, where R' and R" are as defined herein.

As used herein, the term "disulfide" refers to a —S—SR' end group or a —S—S— linking group, as these phrases are defined hereinabove, where R' is as defined herein.

As used herein, the term "carbonyl or carbonate" as used herein, describes a —C(=O)—R' end group or a —C(=O)— linking group, as these phrases are defined hereinabove, with R' as defined herein.

As used herein, the term "thiocarbonyl" as used herein, describes a —C(=S)—R' end group or a —C(=S)— linking group, as these phrases are defined hereinabove, with R' as defined herein.

As used herein, the term "oxime" describes a =N—OH end group or a =N—O— linking group, as these phrases are defined hereinabove.

As used herein, the term "hydroxyl" describes a —OH group.

As used herein, the term "alkoxy" describes both an —O-alkyl and an —O-cycloalkyl group, as defined herein.

As used herein, the term "aryloxy" describes both an —O-aryl and an —O-heteroaryl group, as defined herein.

As used herein, the term "thiohydroxy" describes a —SH group.

As used herein, the term "thioalkoxy" describes both a —S-alkyl group, and a —S-cycloalkyl group, as defined herein.

As used herein, the term "thioaryloxy" describes both a —S-aryl and a —S-heteroaryl group, as defined herein.

As used herein, the term "cyano" describes a —C≡N group.

As used herein, the term "isocyanate" describes an —N=C=O group.

As used herein, the term "nitro" describes an —NO2 group.

As used herein, the term "acyl halide" describes a —(C=O)R"" group wherein R"" is halide, as defined hereinabove.

As used herein, the term "azo" or "diazo" describes an —N=NR' end group or an —N|N— linking group, as these phrases are defined hereinabove, with R' as defined hereinabove.

As used herein, the term "C-carboxylate" describes a —C(=O)—OR' end group or a —C(=O)—O— linking group, as these phrases are defined hereinabove, where R' is as defined herein.

As used herein, the term "O-carboxylate" describes a —OC(=O)R' end group or a —OC(=O)— linking group, as these phrases are defined hereinabove, where R' is as defined herein.

As used herein, the term "C-thiocarboxylate" describes a —C(=S)—OR' end group or a —C(=S)—O— linking group, as these phrases are defined hereinabove, where R' is as defined herein.

As used herein, the term "O-thiocarboxylate" describes a —OC(=S)R' end group or a —OC(=S)— linking group, as these phrases are defined hereinabove, where R' is as defined herein.

As used herein, the term "N-carbamate" describes an R"OC(=O)—NR'— end group or a —OC(=O)—NR'— linking group, as these phrases are defined hereinabove, with R' and R" as defined herein.

As used herein, the term "O-carbamate" describes an —OC(=O)—NR'R" end group or an —OC(=O)—NR'— linking group, as these phrases are defined hereinabove, with R' and R" as defined herein.

As used herein, the term "O-thiocarbamate" describes a —OC(=S)—NR'R" end group or a —OC(=S)—NR'— linking group, as these phrases are defined hereinabove, with R' and R" as defined herein.

As used herein, the term "N-thiocarbamate" describes an R"OC(=S)NR'— end group or a —OC(=S)NR— linking group, as these phrases are defined hereinabove, with R' and R" as defined herein.

As used herein, the term "S-dithiocarbamate" describes a —SC(=S)—NR'R" end group or a —SC(=S)NR'— linking group, as these phrases are defined hereinabove, with R' and R" as defined herein.

As used herein, the term "N-dithiocarbamate" describes an R"SC(=S)NR'— end group or a —SC(=S)NR'— linking group, as these phrases are defined hereinabove, with R' and R" as defined herein.

As used herein, the term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

As used herein, the term "thiourea", which is also referred to herein as "thioureido", describes a —NR'—C(=S)—NR"R'" end group or a —NR'—C(=S)—NR"— linking group, with R', R" and R'" as defined herein.

As used herein, the term "C-amide" describes a —C(=O)—NR'R" end group or a —C(=O)—NR'— linking group, as these phrases are defined hereinabove, where R' and R" are as defined herein.

As used herein, the term "N-amide" describes a R'C(=O)—NR"— end group or a R'C(=O)—N— linking group, as these phrases are defined hereinabove, where R' and R" are as defined herein.

As used herein, the term "guanyl" describes a R'R"NC(=N)— end group or a —R'NC(=N)— linking group, as these phrases are defined hereinabove, where R' and R" are as defined herein.

As used herein, the term "guanidine" describes a —R'NC(=N)—NR"R'" end group or a —R'NC(=N)—NR"— linking group, as these phrases are defined hereinabove, where R', R" and R'" are as defined herein.

As used herein, the term "hydrazine" describes a —NR'—NR"R'" end group or a —NR'—NR"— linking group, as these phrases are defined hereinabove, with R', R", and R'" as defined herein.

As used herein, the term "silyl" describes a —SiR'R"R'" end group or a —SiR'R"— linking group, as these phrases are defined hereinabove, whereby each of R', R" and R'" are as defined herein.

As used herein, the term "siloxy" describes a —Si(OR')R"R'" end group or a —Si(OR')R"— linking group, as these phrases are defined hereinabove, whereby each of R', R" and R'" are as defined herein.

As used herein, the term "silaza" describes a —Si(NR'R")R'" end group or a —Si(NR'R")— linking group, as these phrases are defined hereinabove, whereby each of R', R" and R'" is as defined herein.

As used herein, the term "tetraorthosilicate" describes a —O—Si(OR')(OR")(OR'") end group or a —O—Si(OR')(OR")— linking group, as these phrases are defined hereinabove, with R', R" and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

As used herein, the term "methyleneamine" describes an —NR'—CH2-CH=CR"R'" end group or a —NR'—CH2-CH=CR"— linking group, as these phrases are defined hereinabove, where R', and R'" are as defined herein.

The present disclosure, in some embodiments thereof, relates to sensing and, more particularly, to methods and systems for determining a presence and/or amount of analytes such as, but not limited to, bioanalytes, in a sample such as a biological sample, and to uses thereof. Persons skilled in the art will understand that the present disclosure is not necessarily limited in its application to the details of construction and the arrangement of the components and/or methods set forth in the following description and/or illustrated in the drawings and/or examples. The disclosure is capable of other embodiments or of being practiced or carried out in various ways.

The present invention is directed to the use of a field-effect transistor (FET) in which the electrode of the gate of the transistor acts directly as a working electrode. In the present invention, using the gate's electrode as a working electrode allows for increased sensitivity, specificity, and selectivity by applying varying electrode potentials, and/or any combination thereof. Thus, the applied potential may be tuned to match that of specific redox species to be analyzed. By isolating the gate oxide material from direct interaction with the redox species, using a chemically inert passivation layer, analyte-gate interaction is eliminated, according to some embodiments of the present disclosure. This passivation layer may dramatically reduce ionic, pH and other solution effects, as well as prevent signal drift due to gate surface degradation. Moreover, by using a silicon nanowire (SiNW)-based FET in this setup, according to some embodiments of the present disclosure, superior sensor sensitivity has been demonstrated. According to some embodiments of the present disclosure, the superior sensor sensitivity is achieved due to the SiNW high surface to volume ratio.

Typically, commercially available sensors rely on amperometric measurement such that there is a need to collect sufficient electrons at the working electrode to allow electrical current above the noise level. In contrast, in the present nanowire sensitive FET setup, according to some embodiments of the present disclosure, a small potentiometric change to the working electrode generates a considerable and detectable current change in the adjacent FET, as will be described in further detail below. Thus, the nanowire sensitive FET has a miniaturized footprint, according to some embodiments of the present disclosure, as compared to commercially available electrochemical sensors, allowing the FET to be placed in compact devices, such as, but not limited to, microprobes or minimally-invasive microprobes, aimed at sensing an array of metabolites and other chemicals in interstitial fluid. According to some embodiments of the present disclosure, the sensitivity of such a small footprint sensor is unmatched when compare to existing electrochemical sensors. In addition, according to some embodiments of the present disclosure, another advantage of using such small sensors is the ability to form a sensor array with an area that is smaller than 0.1 mm$^2$, or 0.5 mm$^2$, or 1.0 mm$^2$ or 2.0 mm$^2$, allowing sensing of multiple different analytes in parallel.

In another embodiment, a MOSFET-based technology can be used to substitute the nanowire sensing element, having the metal gate of the MOSFET as the working electrode which is in contact with the analyte solution. In yet another embodiment, CMOSFET-based technology can be used to substitute the nanowire sensing element, having the metal gate of the CMOSFET as the working electrode which is in contact with the analyte solution.

The FET Sensor

According to an aspect of some embodiments of the present disclosure, there is provided a mediator-free, redox-tunable, electrochemical FET-amplified sensing system (FET sensing system) comprising a working electrode, an insulator and a FET amplifier. The FET sensing system, according to embodiments of the present disclosure, is configured to detect the presence and/or amount of an analyte in a sample, for example, a biological sample.

Referring now to the drawings, FIG. 1 is a schematic illustration of a tunable potentiometric redox-FET sensor 100 according to exemplary embodiments of the present disclosure. The FET sensor 100 comprises a gate electrode which is used as a working electrode 102 and a FET amplifier 104 comprising a source terminal 106 connected to a drain terminal 108 by at least one nanowire 110. As depicted in FIG. 1, the FET amplifier 104 is isolated from the working electrode 102 and the analyte solution 120 by a chemical and electrical insulator 114. As shown in the figure, the analyte solution 120 is located in a well 144 defined by well walls 143. This separation of the working electrode 102 from the FET amplifier 104 allows the working electrode 102 to be positioned within an analyte solution 120 in the well 144 without any contact between the FET amplifier 104 and the analyte solution 120. Physiochemically isolating the FET amplifier 104 from the analyte solution 120 by the insulator 114, leaving only the working electrode 102 exposed to the analyte solution 120, enhances the specificity of the FET sensor 100 and at least reduces undesirable FET potential drift, as will be described in further detail below.

In some embodiments of the present invention, the working electrode 102 is a single working electrode connected to a voltage source 124. The working electrode 102, in some embodiments of the present invention, comprises a noble metal such as, for example, gold, platinum, ruthenium, rhodium, palladium, silver, osmium, iridium, or similar noble metals that are very resistant to corrosion such as titanium, tantalum and/or carbons.

The major dimension of the exposed working electrode 102, in some embodiments of the present invention, is approximately 200 micrometers in length. The major dimension is the longest dimension in a viewed plane. For example, the major dimension of a round wire cross section is the cross section circular diameter. The major dimension of a rectangular cross section of an element is the length of the rectangle diagonal. The major dimension of a triangular cross section of an element is the length of the triangle base. In other embodiments, the working electrode 102 major dimension is 1 micron to 10,000 microns, or 100 microns to 10,000 microns, or 750 microns to 10,000 microns, or 1,500 microns to 10,000 microns, or 2,500 microns to 10,000 microns, or 5,000 microns to 10,000 microns, or 7,500 microns to 10,000 microns.

In some embodiments, the working electrode 102 major dimension is 1 micron to 12,000 microns. In other embodiments, the working electrode 102 major dimension is 1 micron to 10,000 microns, or 1 micron to 7,500 microns, or 1 micron to 5,000 microns, or 1 micron to 2,500 microns, or 1 micron to 1,000 microns, or 1 micron to 500 microns, or 1 micron to 250 microns.

In other embodiments, the working electrode 102 major dimension is 50 microns to about 250 microns. In other embodiments, the working electrode 102 major dimension is 100 microns to 750 microns, or 750 microns to 5,000 microns, or 250 microns to 7,000 microns, or 2,500 microns to 3,000 microns, or 1,000 microns to 3,000 microns, or 150 microns to 8,000 microns.

The working electrode 102 is configured to interact with an analyte 118 in the analyte solution 120. Specifically, there is an electron transfer from the analyte 118 to the working electrode 102, which creates an electric field that is detected by the FET amplifier 104. In some embodiments of the present invention, this electron transfer is the result of a redox reaction between the working electrode 102 and the analyte 118.

Figure 3:
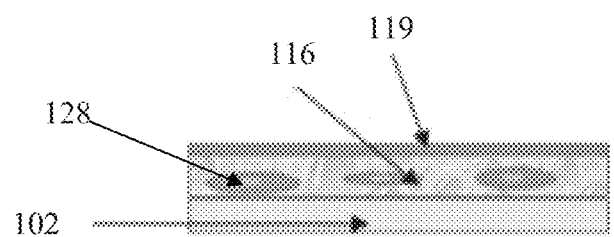
FIG. 3 is a schematic illustration of a working electrode with an enzyme-containing sensing hydrogel according to some embodiments of the present disclosure.

In some embodiments of the present invention, the redox reaction occurs because of an enzyme-containing sensing hydrogel 116 deposited on the working electrode 102, as shown in FIG. 3. Specifically, the sensing hydrogel 116 and the amount of enzyme in the hydrogel is selected such that, upon contacting an analyte 118 in the analyte solution 120, a redox molecule is produced resulting in a shift of the working electrode potential.

As defined herein, a "hydrogel" is a three-dimensional fibrous network containing at least 20%, or at least 50%, or at least 80%, and up to about 99.99% (by mass) water. A hydrogel can be regarded as a material which is mostly water, yet behaves like a solid or semi-solid due to a three-dimensional crosslinked solid-like network, made of natural and/or synthetic polymeric chains, within the liquid dispersing medium. According to some embodiments of the present disclosure, a hydrogel may contain polymeric chains of various lengths and chemical compositions depending on the precursors used for preparing it. The polymeric chains can be made of monomers, oligomers, block-polymeric units, which are inter-connected (crosslinked) by chemical bonds (covalent, hydrogen and ionic/complex/metallic bonds, typically covalent bonds.)

Exemplary polymers or co-polymers usable for forming the sensing hydrogel 116 according to the present embodiments include polyacrylates, polyhydroxyethylmethacrylate, polymethacrylates, polyacrylamides, polymethacrylamides, polyvinylpyrrolidone and copolymers of any of the foregoing. Other examples include polyethers, polyurethanes, functionalized polyethylene glycol), redox hydrogel (such as Os-complex based redox hydrogel), and macromers.

In some embodiments of the present invention, the sensing hydrogel 116 is adhered to the working electrode 102 via an optional adhesive layer (not shown). Some examples of adhesive layers include, but are not limited to, polyurethane, self-assembled monolayers, or combinations thereof.

The sensing hydrogel 116, in some embodiments of the present invention, includes at least one type of enzyme 128 that interacts with a specific corresponding analyte 118 to be sensed in the analyte solution 120. For example, in some embodiments of the present invention, the enzyme within the sensing hydrogel 116 includes glucose oxidase, lactate oxidase, cholesterol oxidase, pyruvate oxidase, Glycerol oxidase, Alcohol oxidase, Glutaminase oxidase, L-glutamate oxidase, Xanthine oxidase, L-glutamate oxidase, Choline oxidase, Sarcosine oxidase and Ascorbate oxidase or Creatininase, Creatinase, Peroxidase, Laccase, Tyrosinase or 3-hydroxybutyrate dehydrogenase, Glucose dehydrogenase, Lactate dehydrogenase, Alcohol dehydrogenase, Glutamate dehydrogenase. The enzyme is selected so that the enzyme interacts with the specific analyte 118, such as, for example, β-d-Glucose, L-lactate, Glutamine, cholesterol, Glycerol, pyruvate, Ethanol L-glutamate, Choline Acetylcholine, l-Ascorbic acid, cortisol, Creatine, Creatinine, 2-hydroxybutyrate or 3-hydroxybutyrate, to form an electron transport cofactor, such as, for example, hydrogen peroxide, nicotinamide adenine dinucleotide (NADH), flavin adenine dinucleotide (FAD) and flavin mononucleotide (FMN) and quinone cofactors. The cofactors may be inorganic, such as iron-sulfur clusters, or organometallic such as hemes. Thus, in these embodiments, the formation of the electron transport cofactor creates the electrical shift in the working electrode potential, resulting in a change the surrounding electrical field that affects the FET amplifier 104. Mediators such as ferricyanide and ferrocene, methylene blue, phenazines, methyl violet, alizarin yellow, Prussian blue, thionin, azure A and C, toluidine blue and inorganic redox ions, can be added to the sample or immobilized on the electrode surface.

In some embodiments of the present invention, additional limiting membrane(s) can also be deposited on the working electrode 102 to provide control of the diffusion rate and/or concentration of an analyte 118. In some embodiments of the present invention, the limiting membranes are semi-permeable membranes 119 such as Nafion, Cellulose Acetate, Polypyrrole, Polyurethane, Chitosan, Poly(2-hydroxyethyl methacrylate), HAs/poly(diallyldimethylammonium chloride) (PDDR) and polystyrene sulfonate) (PSS)/PDDA These semi-permeable membranes 119 can also diminish detection of interfering species such as, for example, uric acid, lactic acid, ascorbic acid, acetaminophen and oxygen.

In some embodiments of the present invention, an antifouling layer such as cellulose acetate biocides embedded in a copolymer matrix, polymers containing phosphorylcholine (PC)-substituted methacrylate units, antimicrobial N-halamine polymer, fluoroalkyl diol-containing polyurethanes, poly(ether) grafted poly(urethanes), and plasma polymers of hexamethyldisiloxane/O2, epoxy resins, Nafion, polypeptides, polyethylene glycol PEG), polyglycerol (PG), polysaccharides, polyoxazoline, polypropylene sulfoxide), 2-Methacryloy-loxyethyl Phosphorylcholine (MPC), poly (phosphoester), vinylpyrrolidone, polyvinyl alcohol) (PVA) and zwitterionic polymers such as phosphorylcholine, poly (carboxy-betaine acrylamide) (pCBAA) and sulfobetaine or carboxybetaine polymers can be used to prevent clogging and disruption of analyte diffusion into the sensing hydrogel 116.

Turning back to FIG. 1, the FET amplifier 104 includes a source terminal 106 and a drain terminal 108 connected by at least one nanowire 110. In proximity to the electric field of the working electrode 102, there is a continuous flow of current from the source terminal 106 to the drain terminal 108 across the at least one nanowire 110. However, changes in the surrounding electrical field by, for example, redox species produced by enzymatic redox reaction of bioanalyte by enzymes 128 contained in the sensing hydrogel 116 on top of the working electrode 102 and in contact with the semi-permeable membrane 119 and with the analyte 118, may result in an increase or a decrease in the electric current flowing across the at least one nanowire 110.

In some embodiments of the present invention, a plurality of nanowires may be used. When a plurality of nanowires is employed, the nanowires are, in some embodiments of the present invention, arranged in an array. For example, the nanowires can be arranged generally parallel to each other. In some embodiments of the present invention, the FET amplifier may include from 1 nanowire to 100 nanowires, or from 1 nanowire to 90 nanowires, or from 1 nanowire to 90 or from 1 nanowire to 75 nanowires, or from 1 nanowire to 60 nanowires, or from 1 nanowire to 45 nanowires, or from 1 nanowire to 25 nanowires, or from 1 nanowire to 10 nanowires, or from 1 nanowire to 5 nanowires.

In some embodiments of the present invention, the FET amplifier may include from 5 nanowires to 100 nanowires, or from 15 nanowires to 100 nanowires, or from 30 nanowires to 100 nanowires, or from 40 nanowires to 100 nanowires, or from 55 nanowires to 100 nanowires, or from 70 nanowires to 100 nanowires, or from 85 nanowires to 100 nanowires, or from 95 nanowires to 100 nanowires.

In some embodiments of the present invention, the FET amplifier may include from 15 nanowires to 65 nanowires, or from 2 nanowires to 7 nanowires, or from 10 nanowires to 15 nanowires, or from 12 nanowires to 25 nanowires, or from 35 nanowires to 55 nanowires.

In some embodiments of the present invention, the at least one nanowire 110 has a circular cross section with an average diameter of from 1 nanometer to 500 nanometers, or from 50 nanometers to 500 nanometers, or from 150 nanometers to 500 nanometers, or from 200 nanometers to 500 nanometers, or from 250 nanometers to 500 nanometers, or from 375 nanometers to 500 nanometers, or from 450 nanometers to 500 nanometers.

In some embodiments, the average diameter of the circular cross section is from 1 nanometer to 450 nanometers, or from 1 nanometer to 400 nanometers, or from 1 nanometer to 300 nanometers, or from 1 nanometers to 250 nanometers, or from 1 nanometer to 200 nanometers, or from 1 nanometer to 150 nanometers, or from 1 nanometer to 100 nanometers, or from 1 nanometer to 50 nanometers.

In some embodiments, the average diameter of the circular cross section is from 10 nanometers to 50 nanometers, or from 150 nanometers to 400 nanometers, or from 50 nanometers to 300 nanometers, or from 100 nanometers to 250 nanometers, or from 200 nanometers to 250 nanometers, or from 100 nanometers to 150 nanometers, or from 400 nanometers to 450 nanometers, or from 350 nanometers to 450 nanometers.

Figure 2:
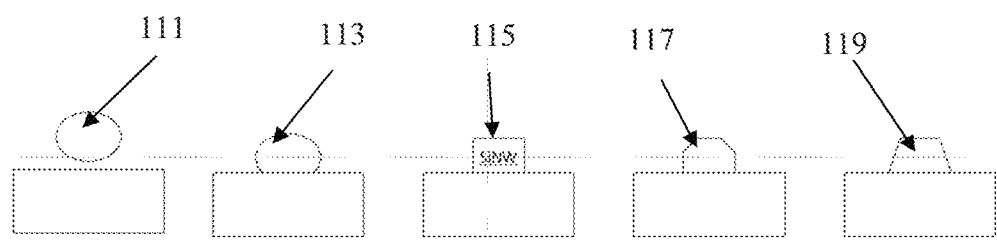
FIG. 2 is a schematic illustration of exemplary cross-sectional shapes of a nanowire of the SiNW FET sensor of FIG. 1, according to some embodiments of the present disclosure.

In some embodiments of the present invention, the at least one nanowire 110 may have a non-circular cross-section. For example, the cross-section of the at least one nanowire 110 may have any arbitrary shape, including, but not limited to, circular, square, rectangular, elliptical and tubular. In some embodiments of the present invention, the at least one nanowire 110 may have a regular or irregular shaped cross-section. FIG. 2 depicts some exemplary cross-sections of the at least one nanowire 110 according to embodiments of the present disclosure. For example, the nanowires may include, but are not limited to, oval 111, semi-oval 113, rectangular 115, hexagonal 117 or trapezoidal 119.

In some embodiments of the present invention, the at least one nanowire 110 has a non-circular cross-sectional major dimension of 5 nanometers to 1000 nanometers, or 25 nanometers to 1000 nanometers, or 50 nanometers to 1000 nanometers, or 75 nanometers to 1000 nanometers, or 100 nanometers to 1000 nanometers, or 150 nanometers to 1000 nanometers, or 200 nanometers to 1000 nanometers, or 300 nanometers to 1000 nanometers, or 500 nanometers to 1000 nanometers, or 700 nanometers to 1000 nanometers, or 800 nanometers to 1000 nanometers, or 900 nanometers to 1000 nanometers.

In some embodiments, the at least one nanowire 110 has a non-circular major dimension of 5 nanometers to 900 nanometers, or 5 nanometers to 800 nanometers, or 5 nanometers to 700 nanometers, or 5 nanometers to 600 nanometers, or 5 nanometers to 500 nanometers, or 5 nanometers to 400 nanometers, or 5 nanometers to 300 nanometers, or 5 nanometers to 200 nanometers, or 5 nanometers to 150 nanometers, or 5 nanometers to 100 nanometers, or 5 nanometers to 50 nanometers, or 5 nanometers to 25 nanometers, or 5 nanometers to 10 nanometers.

In some embodiments, the at least one nanowire 110 has a non-circular major dimension of 10 nanometers to 100 nanometers, or 25 nanometers to 75 nanometers, or 250 nanometers to 750 nanometers, or 300 nanometers to 500 nanometers, or 100 nanometers to 400 nanometers, or 50 nanometers to 150 nanometers.

In some embodiments of the present invention, the at least one nanowire 110 has a length in the range of 1 micron to 500 microns. As defined herein, a length is a dimension of the at least one nanowire extending from a first end connected to the source terminal 106 to a second end connected to the drain terminal 108. In some embodiments of the present invention, the at least one nanowire 110 has a length in the range of 10 microns to 500 microns, or 50 microns to 500 microns, or 100 microns to 500 microns, or 150 microns to 500 microns, or 200 microns to 500 microns, or 250 microns to 500 microns, or 300 microns to 500 microns, or 400 microns to 500 microns.

In some embodiments of the present invention, the at least one nanowire 110 has a length in the range of 1 micron to 400 microns, or 1 micron to 300 microns, or 1 micron to 250 microns, or 1 micron to 200 microns, or 1 micron to 100 microns, or 1 micron to 50 microns, or 1 micron to 25 microns, or 1 micron to 10 microns.

In some embodiments of the present invention, the at least one nanowire 110 has a length in the range of 10 microns to 50 microns, or 50 microns to 150 microns, or 25 microns to 100 microns, or 300 microns to 400 microns, or 75 microns to 200 microns, or 5 microns to 75 microns.

To increase electrical field sensitivity, the FET amplifier 104, in some embodiments of the present disclosure, includes silicon nanowires (SiNW). In some embodiments of the present disclosure, the SiNVVs respond to minor changes in the surrounding electrical field because of their significantly high surface area to volume ratio. For example, assuming a half cylinder shaped nanowire, wherein the flat portion of the nanowire is in contact with a substrate, the half cylinder radius, R, is 50 nanometers (nm), and the nanowire length, L, is 10 microns, that is, 10000 nanometers. The half cylinder nanowire volume is $V=Pi/2*R^2*L$ and the half cylinder surface area is $S=2*Pi/2*R*L$. The surface area to volume ratio is Ratio (Surface area/Volume)=$2/R$=$1/25$=0.04 $nm^{-1}$.

In another example, assuming a nanowire with a square-shaped cross section, wherein the square side length, SL, is 50 nm, and the nanowire length, L, is 10 microns, that is, 10,000 nm. The nanowire volume is $V=SL^2*L$ and the nanowire surface area not in contact with the substrate, that is three faces of the rectangular element, is $S=3*SL*L$. The surface area to volume ratio is Ratio (Surface area/Volume) =$3/SL$=$3/50$=0.06 $nm^{-1}$.

In an embodiment, the surface area to volume ratio (Surface area/Volume) is smaller than 1.000 $nm^{-1}$, or smaller than 0.800 $nm^{-1}$, or smaller than 0.500 $nm^{-1}$, or smaller than 0.250 $nm^{-1}$, or smaller than 0.100 $nm^{-1}$, or smaller than 0.080 $nm^{-1}$, or smaller than 0.040 $nm^{-1}$, or smaller than 0.020 $nm^{-1}$, or smaller than 0.010 $nm^{-1}$, or smaller than 0.005 $nm^{-1}$, or smaller than 0.003 $nm^{-1}$, or smaller than 0.002 $nm^{-1}$. Thus, changes in the source-drain electric current (lsd) flow occur with minimal losses, providing superior sensor sensitivity.

In some embodiments of the present invention, the at least one nanowire 110 may by suspended above the substrate, as depicted in FIG. 2.

Figure 9:
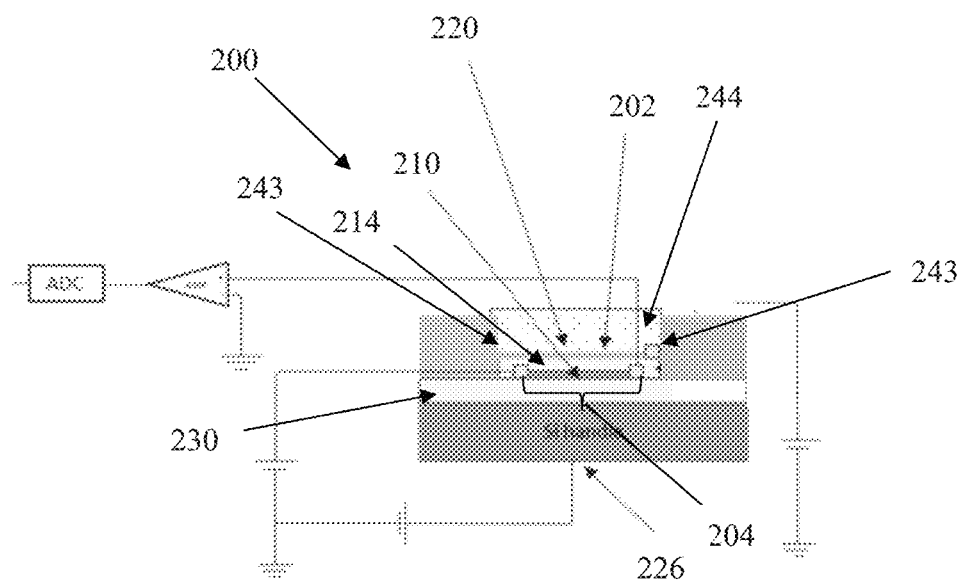
FIG. 9 is a schematic illustration of an exemplary SiNW FET sensor according to some embodiments of the present disclosure.

In some embodiments of the present invention, unlike typical FET sensors, the at least one nanowire 110 of the current FET sensor 100 are not in contact with the analyte 118, as will be described in further detail below, providing numerous performance advantages, as well as flexibility of the system design. In some embodiments of the present invention, the surfaces of the at least one nanowire 110 are chemically passivated. In some embodiments of the present invention, the surfaces of the at least one nanowire 110 are chemically passivated and reduce electrical noise resulting from the analyte solution 120. In other embodiments, the at least one nanowire is encapsulated. In other embodiments, the at least one nanowire is encapsulated and is electrically and chemically isolated and protected from the environment or solution. In other embodiments, the at least one nanowire 110 is encapsulated with a coating of metal oxides, polymers and/or other insulators. In some embodiments, encapsulation of the at least one nanowire 110 results in separation of the signal of the working electrode 102 and by-signals which may occur from direct contact of the analyte 118 with the at least one nanowire 110, as well as chemical modification of the sensitive surface of the at least one nanowire 110. Also, by virtue of encapsulating the at least one nanowire 110 in a stacked configuration, the working electrode 120 can be placed on top of the at least one nanowire 110, allowing for reduction in form factor, as shown in FIG. 9 and described below.

In an embodiment, the encapsulation is achieved by covering the at least one nanowire with an insulator. In an embodiment, the at least one covered nanowire is embedded within an insulator.

As shown in FIG. 1, in some embodiments of the present invention, the FET sensor 100 further includes a back gate electrode 126 which allows for tuning of the voltage applied to the working electrode 102. The back gate electrode 126, in this embodiment, is a silicon based electrode. As shown in FIG. 1, the back gate electrode 126 is separated from the FET amplifier 104 by a dielectric oxide layer 130, which is positioned below, and provides support to, the FET amplifier 104. Selectivity of the FET sensor 104 can be tuned using the back gate electrode 126 to specifically sense different redox species by applying different voltage settings to the working electrode 102. Furthermore, physiochemically isolating the back gate electrode 126 from the analyte solution 120 by the dielectric oxide layer 130 further enhances specificity of the FET sensor 100 and eliminates undesirable redox potential drift.

FIGS. 4-7 depict the general mechanism of action of the FET sensor 100, in some embodiments of the present invention. Specifically, interaction of a redox species with the disclosed device forms a specific work function (WF), in units of eV, with respect to the working electrode 102. This leads to one of three possible outcomes, depending on the working electrode initial potential bias. The first possible outcome occurs when the WF and applied working electrode potential are equal ($\phi WF = \phi WE$). Here, the overall electric potential will not change, resulting in no change to the adjacent FET lsd.

Figure 4:
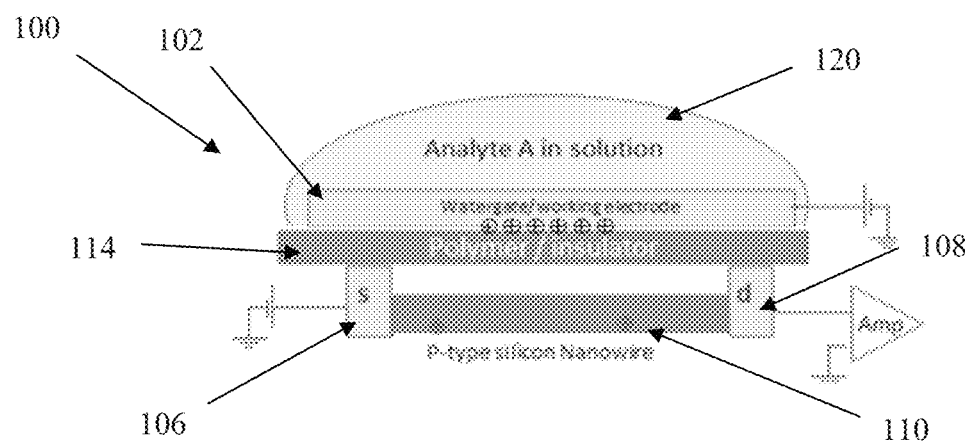
FIG. 4 is a schematic illustration of a SiNW FET system used in experiments performed according to some embodiments of the present disclosure.
Figure 5:
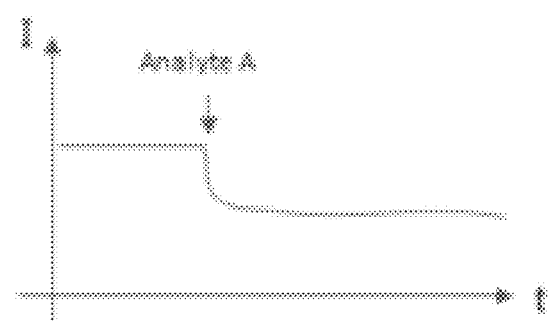
FIG. 5 is a graph of the change in current across a nanowire of the SiNW FET system in response to a redox reaction according to some embodiments of the present disclosure.

The second possible outcome occurs when the WF is higher than the applied working electrode potential ($\phi WF > \phi WE$). In this situation, the overall electric potential will add up, resulting in reduced lsd in a P-type semiconductor, and increased lsd in an N-type semiconductor. FIGS. 4-5 depict the second scenario in which the lsd is reduced in the P-type semiconductor—i.e., the at least one nanowire 110. In this configuration, analyte A leads to positive polarization of the working electrode, resulting in depletion of free charge carriers (+) at the adjacent P-type silicon nanowires 110, thereby decreasing the electric current flowing through the drain terminal 108. This decrease in electric current is shown in the graph of FIG. 5.

Figure 6:
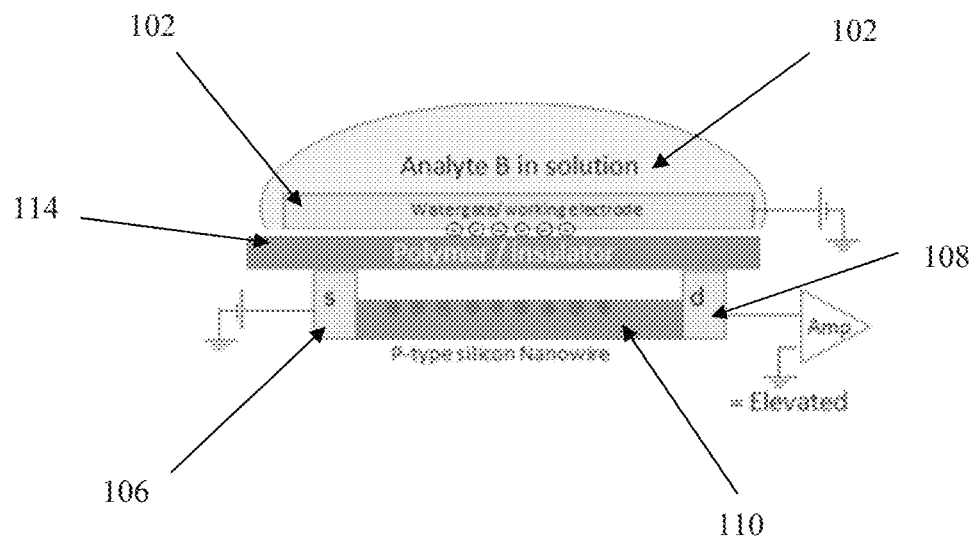
FIG. 6 is another schematic illustration of a SiNW FET system used in experiments performed according to some embodiments of the present disclosure.
Figure 7:
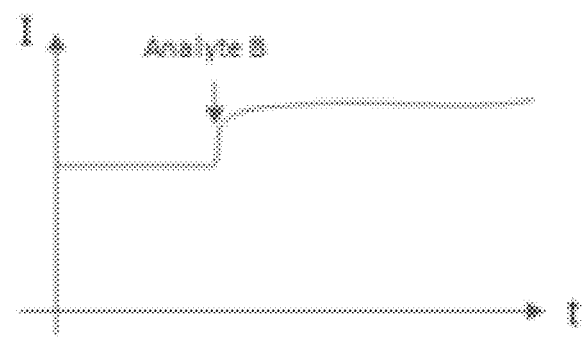
FIG. 7 is a graph of the change in current across a nanowire of the SiNW FET system in response to a redox reaction according to some embodiments of the present disclosure.

The third possible outcome occurs when the WF is lower than the applied working electrode potential $\phi WF < \phi WE$). In this situation, the overall electric potential will represent the difference between working electrode 102 and WF, resulting in increased lsd in a P-type semiconductor, and reduced lsd in an N-type semiconductor. FIGS. 6-7 depicts this third scenario in which the lsd is increased in the P-type semiconductor—i.e., the silicon nanowire 110. In this configuration, the analyte B causes a negative polarization of the working electrode 102, resulting in an accumulation of free charge carriers (+) at the adjacent silicon nanowires 110, thereby increasing the electric current flowing through the drain terminal 108. This increase in electric current is shown in the graph of FIG. 7.

The disclosed setup of the FET sensor 100, as noted before, has superior sensor sensitivity, in part due to the use of silicon nanowires. While commercially available sensors rely on amperometric measurement, where there is a need to collect a sufficient number of electrons at the working electrode to provide an electrical current signal that is above the electrical noise level. Furthermore, commercially available sensors typically require at least two electrodes in contact with the analyte solution, which results in increased electrical noise and, also increases the sensor's dimensions. For example, typical commercially available sensors are approximately 10 mm in length. In contrast, in the silicon nanowire-sensitive FET sensor 100, a small potentiometric change to the working electrode 102 generates a considerable current elevation in the adjacent FET amplifier 104. Because of this increased current elevation, as compared to amperometric sensors, in some embodiments of the present invention, the FET sensor 100 may have a miniaturized footprint of about 0.0025 mm² (0.05×0.05 mm). In other embodiments, the FET sensor 100 has a miniaturized footprint of 0.00005 mm² to 0.005 mm², or 0.00006 mm² to 0.005 mm², or 0.0001 mm² to 0.005 mm², or 0.0005 mm² to 0.005 mm², or 0.001 mm² to 0.005 mm².

In other embodiments, the FET sensor 100 may have a miniaturized footprint of 0.00005 mm² to 0.001 mm², or 0.00005 mm² to 0.0005 mm², or 0.00005 mm² to 0.0001 mm², or 0.00005 mm² to 0.00006 mm².

In other embodiments, the FET sensor 100 may have a miniaturized footprint of 0.0001 to 0.001 mm², or 0.0025 to 0.0005 mm², or 0.0006 to 0.001 mm².

In some embodiments, the FET sensor 100 has a miniaturized major length of length of about 0.2 mm. In other embodiments, the FET sensor 100 has a miniaturized major length of 0.1 mm to 1.5 mm, or 0.1 mm to 1.3 mm, or 0.1 mm to 1.1 mm, or 0.1 mm to 0.9 mm, or 0.1 mm to 0.7 mm, or 0.1 mm to 0.5 mm, or 0.1 mm to 0.3 mm.

In some embodiments, the FET sensor 100 has a miniaturized major length of 0.3 mm to 1.5 mm, or 0.5 mm to 1.5 mm, or 0.7 mm to 1.5 mm, or 0.9 mm to 1.5 mm, or 1.1 mm to 1.5 mm, or 1.3 mm to 1.5 mm.

Figure 8:
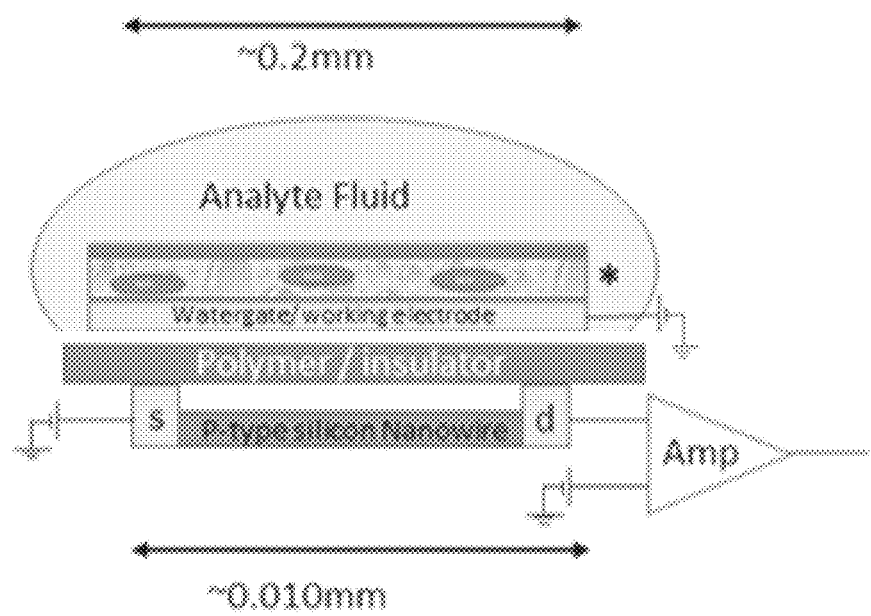
FIG. 8 is a schematic illustration of an exemplary SiNW FET sensor according to some embodiments of the present disclosure.

In other embodiments, the FET sensor 100 has a miniaturized major length of 0.3 mm to 1.1 mm, or 0.7 mm to 0.9 mm, or 0.9 mm to 1.3 mm, or 0.5 mm to 1.1 mm, or 0.3 mm to 0.5 mm, or 0.5 mm to 1.1 mm, or 0.7 mm to 1.3 mm. The major length of the FET sensor 100 allows the FET sensor 100 to be placed in compact devices, such as microprobes or minimally-invasive microprobes aimed at sensing multiple different metabolites and other chemicals in the interstitial fluid. The miniaturized size of the current FET sensor 100 can be seen in FIG. 8.

FIG. 9 depicts a compact, layered design, of a tunable potentiometric redox-FET sensor 200, in some embodiments of the present invention, with a reduced form factor due to the covering of the at least one nanowire 210 with the chemical and electrical insulator 214. In this embodiment, at least one silicon nanowire (SiNW) 210 is connected to a source terminal and a drain terminal to form the FET amplifier 204, similar to FET amplifier 104. However, in this embodiment, the FET amplifier 204, working electrode 202 and chemical and electrical insulator 214 are in a stacked configuration. Specifically, the working electrode 202 is stacked over the insulator 214, which is stacked over the FET amplifier 204. Insulator 214 separates the FET amplifier 204 from the working electrode 202 and from the analyte solution 220 in the well 244. The well is defined by polymeric well walls 243, as shown in the figure. Additionally, the FET sensor 200, in this embodiment, the back gate electrode 226 and the dielectric oxide layer 230 are positioned under both the FET amplifier 204, as shown in FIG. 9, providing a more compact sensor design and reduction in form factor.

Calibration of the FET Sensor

One objective of the calibration process in the present invention is to identify a voltage value or voltage value range in which the performance of the working electrode will be robust and sufficiently sensitive. In some cases, the calibration process also identifies the voltage value or voltage value range of the back gate electrode that will support this performance level of the working electrode.

The calibration process, in some embodiments of the present invention, may be required for various reasons. For example, in some instances, where multiple FET sensors are being used, there may be differences between devices from different manufacturing lots. Also, within the same manufacturing lot there may be differences in sensor performance. In other instances, calibration may be required when working with multiple sensors whose performance curves have similar shapes but may be shifted in some manner. Furthermore, in some cases, sensor performance may drift due to natural material degradation or to environmental or external factors, which can be accounted for by calibration.

In one aspect of the present invention, a robust sensor performance results in the sensor being capable of identifying a target analyte, repeatedly and consistently and is insensitive to other materials and noise. In another aspect of the present invention, the calibration process is based on identifying a singularity point in the performance graph of a sensor for a given analyte. A singularity point may be a voltage value or small voltage range in which the sensor's response to a specific analyte (i.e., change in lsd current) is minimized or becomes unnoticeable.

In some embodiments of the present invention, the sensor's sensitivity to a specific analyte will increase as the voltage level is increased or reduced from the voltage value at the singularity point. In an example, a singularity point can be identified as a peak or valley in the response graph. To the sides of the peak or valley, the response is highly sensitive. This can be seen for example, in an analysis of the first derivative of the response graph. At the peak or valley, the value of the first derivative is zero. To the sides of the peak or valley, the absolute value of the first derivative is greater than zero. That is, the sensor's response is enhanced. Thus, for high sensitivity, the working electrode voltage will be preferentially set at a value that is equal to the singularity point voltage +/− an offset voltage level.

In an exemplary embodiment, the calibration process includes two modes. A "coarse calibration mode," in which identification of the singularity point voltage is achieved by changing the back gate voltage for a given working electrode voltage, and a "fine-tuning calibration mode," in which identification of the singularity point voltage is achieved by changing the working electrode voltage, for a given, fixed back gate voltage. However, there may be interactions between the two modes, such that the sequence of the calibration modes is significant. The final determination of the singularity point voltage should be done with the fine-tuning mode, for a given, fixed back gate voltage.

Once the singularity point potential has been determined, an offset voltage is applied to the back-gate voltage and to the working electrode voltage. The offset voltage levels and direction is also analyte specific and is determined empirically through experimentation. For example, in one embodiment of the present invention, in the case of hydrogen peroxide sensing, a typical working electrode offset would be approximately +/−−0.2 to 0.5 v and a typical back gate offset would be approximately +/−0.5 to 1 v. These offsets will provide robustness and sensitivity to sensor performance, that is, a consistent high response to the desired analyte.

Figure 10:
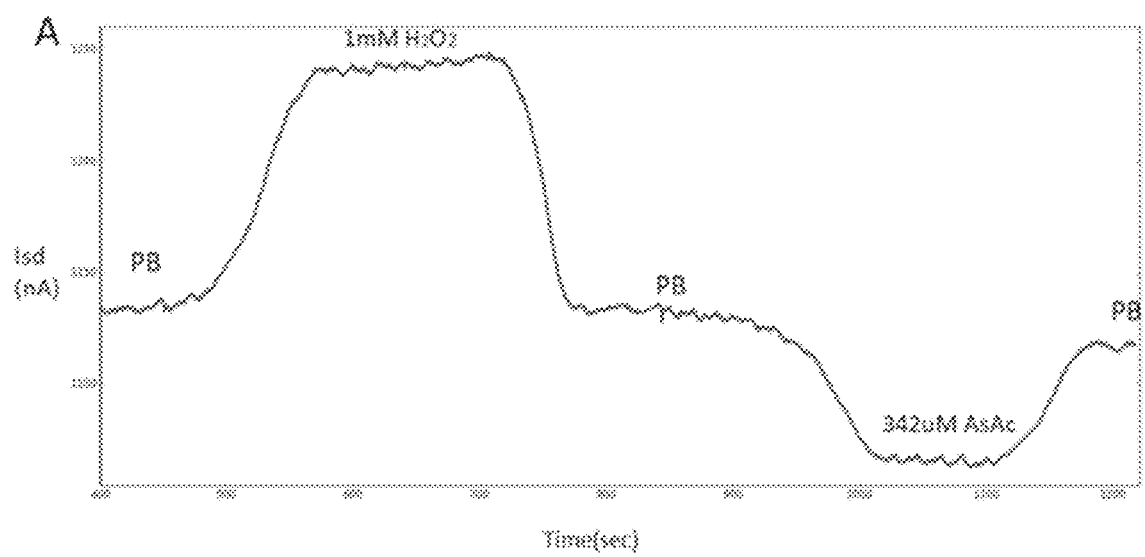
FIG. 10 is a graph of an lsd electric current when an exemplary FET sensor, according to some embodiments of the present disclosure, is introduced to 1 mM hydrogen peroxide and 342 µM ascorbic acid solutions.
Figure 11:
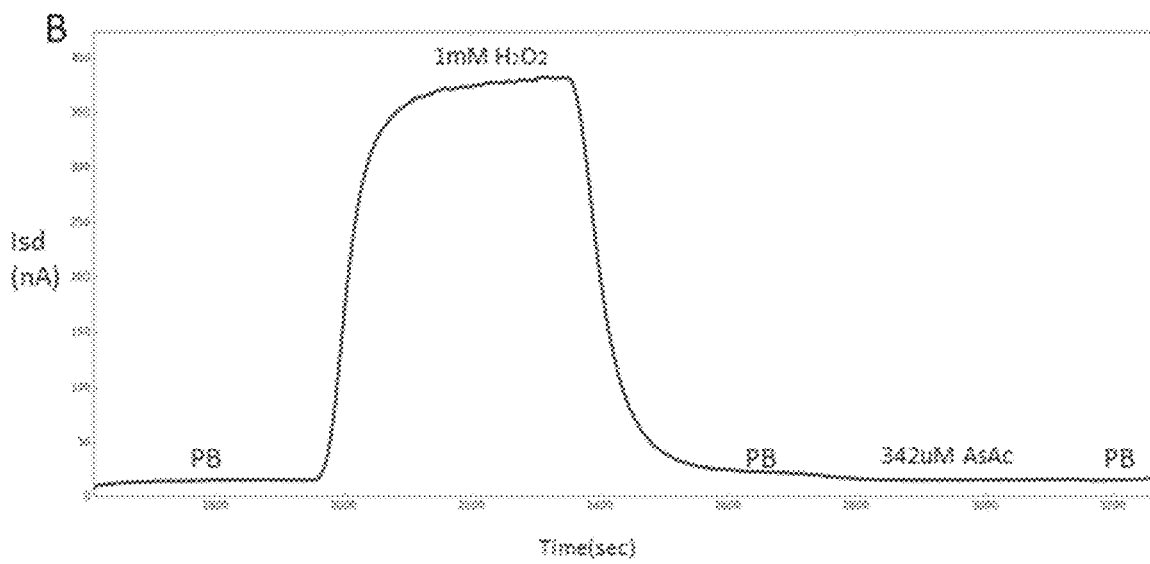
FIG. 11 is a graph of an lsd electric current when an exemplary FET sensor, according to some embodiments of the present disclosure, tuned to tune out ascorbic acid redox signals, is introduced to 1 mM hydrogen peroxide and 342 µM ascorbic acid solutions.

FIGS. 10-11 provide an example of the way proper tuning of a sensor provides filtering of possibly interfering substances or chemical species so that only the substance of interest is being detected in an analyte solution, in some embodiments of the present invention. Specifically, FIGS. 10-11, in one example, demonstrate how to prevent interference from ascorbic acid redox. Metgraphs of FIG. 10 and FIG. 11 show the lsd electric current recordings of the same device when introduced to 1 mM hydrogen peroxide and 342 uM ascorbic acid solutions. However, the back gate voltage (VBg) and working electrode voltage (VWE) are different. In FIG. 10, VBg=−1 v, VWE=−0.2. Using these settings, the presence of hydrogen peroxide leads to an elevated current level while the sensor's response to ascorbic acid was diminished.

Figure 12:
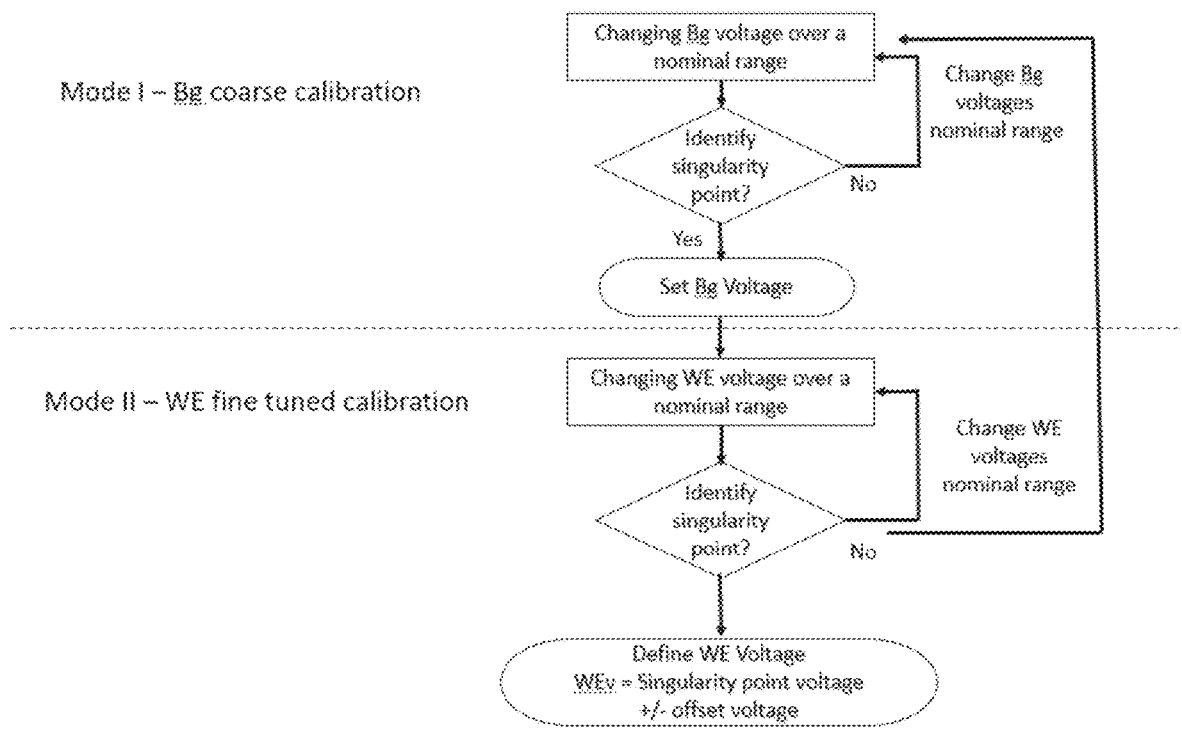
FIG. 12 is a flow chart of an exemplary process for calibrating a FET sensor according to some embodiments of the present disclosure.

FIG. 12 is a flow chart of an exemplary calibration process, in some embodiments of the present invention. In Mode I, the back gate coarse calibration mode, the back gate voltage is changed, while the working electrode voltage is held constant. At each back gate voltage setting, the response is reviewed until a singularity point is identified. The back gate working voltage is then set to a voltage level that is equal to the voltage level at which the singularity point is identified +/− a voltage offset. Once the back gate coarse calibration has been completed, fine-tuning calibration of the working electrode voltage may commence.

In Mode II, separated from Mode I in FIG. 12 by the horizontal dotted line, the fine-tuning calibration of the working electrode is performed by changing the working electrode voltage while the back gate voltage is held constant. At each working electrode voltage setting, the response is analyzed until a singularity point is identified. The working electrode voltage is then set to a voltage level that is equal to the voltage level at which the singularity point was identified with +/− a voltage offset.

In some cases, a partial calibration, including only the working electrode fine tuning calibration, may be sufficient. For example, if the sensor has been calibrated in the past and is due for a periodic calibration, if there is an operational motivation to verify the performance of a working sensor, or if there is a concern that there is a degradation in the functionality of the sensor components. The back gate coarse calibration may be applied primarily on new sensors or in situations in which the singularity point cannot be identified with the working electrode fine tuning calibration procedure.

Figure 13:
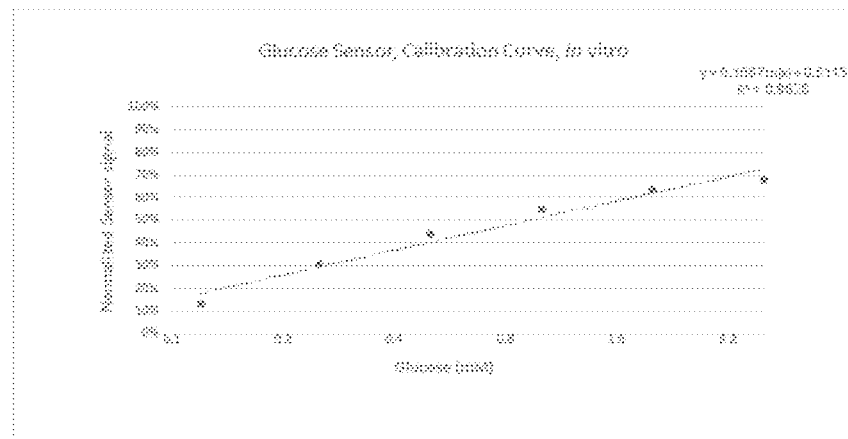
FIG. 13 is a graph of the calibrated response of a SiNW FET glucose sensor, according to some embodiments of the present disclosure, under in vitro conditions.

FIG. 13 depicts a graph of a calibrated response of, in this example, a glucose sensor under in vitro conditions for different glucose concentrations (in phosphate buffer), in some embodiments of the present invention. As can be seen, the graph is linear for the $\log^2$ of glucose concentration with the current increasing as the concentration increases, indicating a normalized sensor signal.

Figure 14:
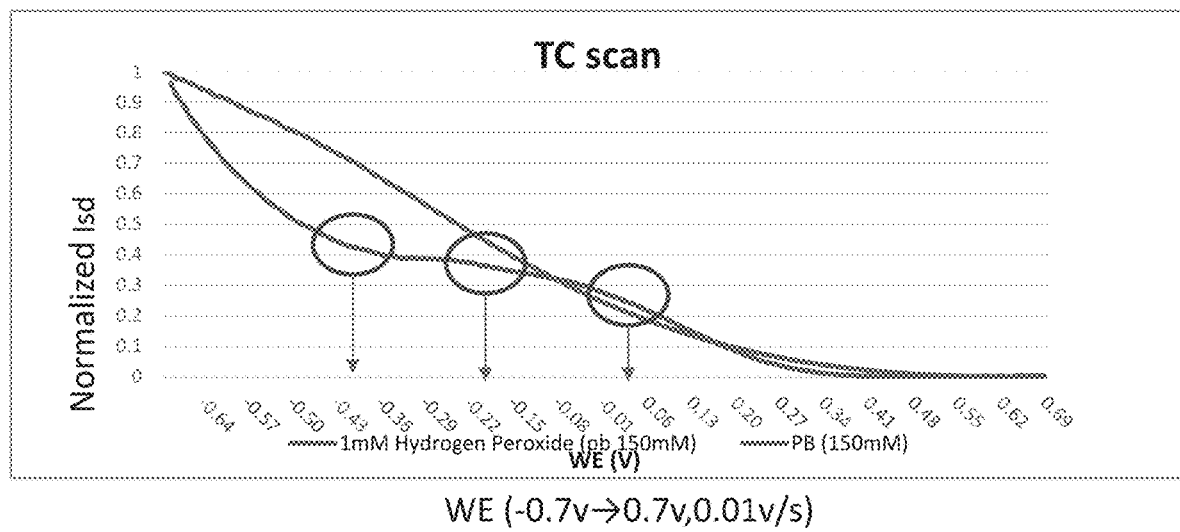
FIG. 14 is a graph of the response of a SiNW FET sensor, according to some embodiments of the present disclosure, to a phosphate buffer at different working electrode voltages.
Figure 15:
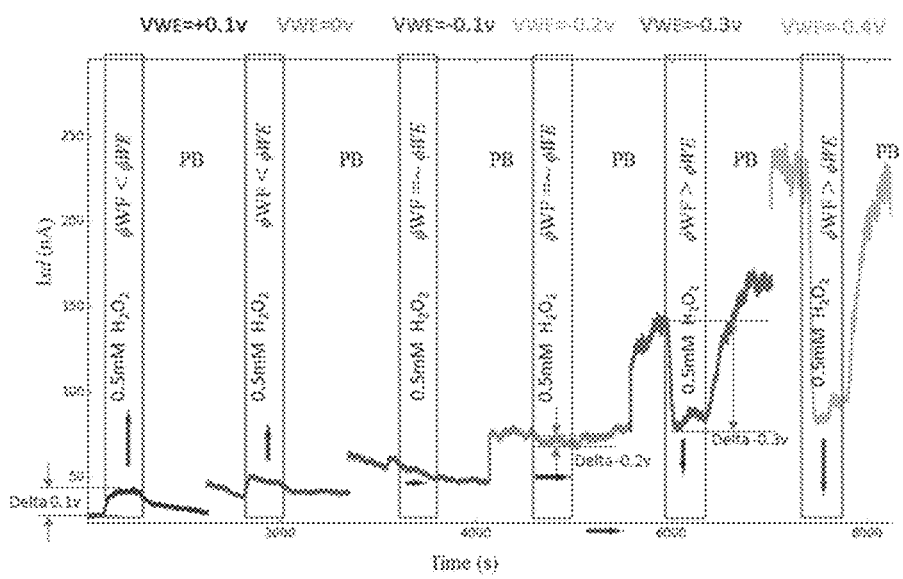
FIG. 15 is a graph of the response of a SiNW FET sensor to hydrogen peroxide at different working electrode voltages.
Figure 16:
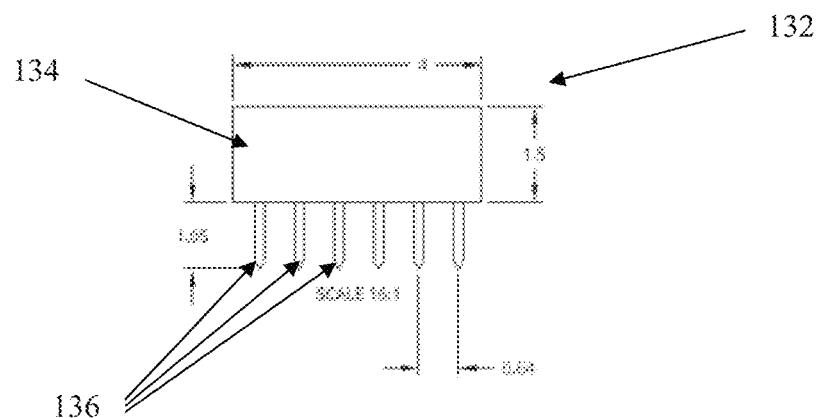
FIG. 16 is a schematic illustration of a multi-microprobe sensing chip according to some embodiments of the present disclosure.
Figure 17:
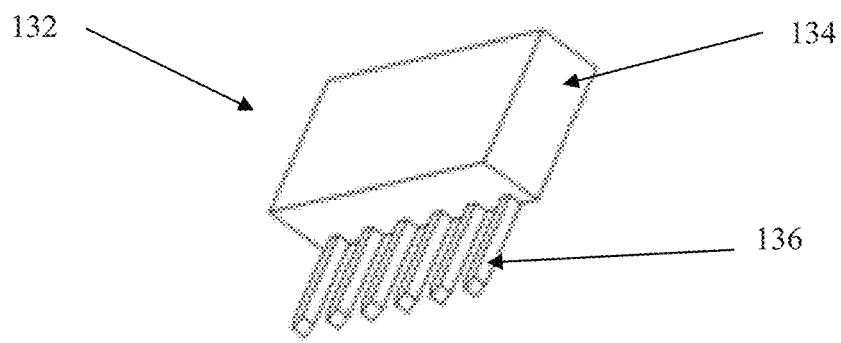
FIG. 17 is a perspective view of a multi-microprobe sensing chip according to some embodiments of the present disclosure.
Figure 18:
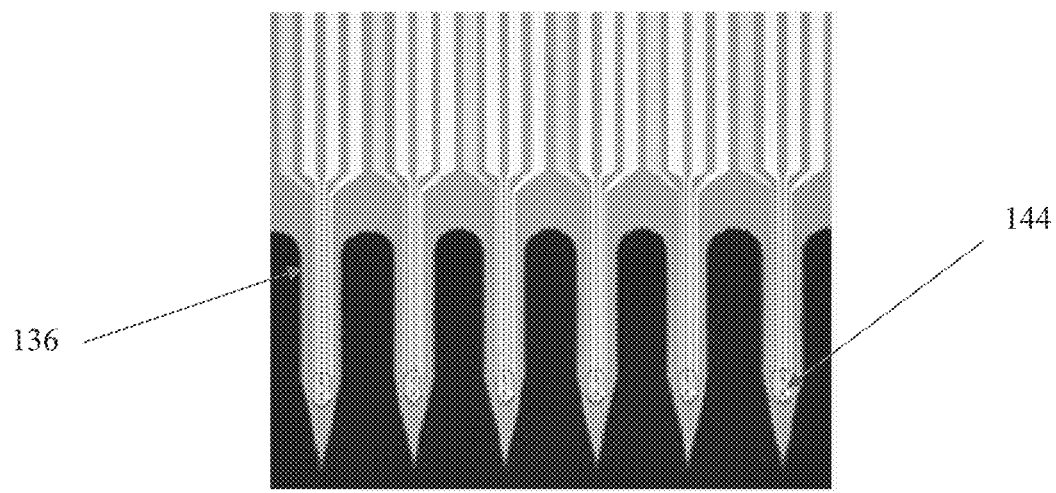
FIG. 18 is a magnified view of microprobes of a multi-microprobe sensing chip according to some embodiments of the present disclosure.
Figure 19:
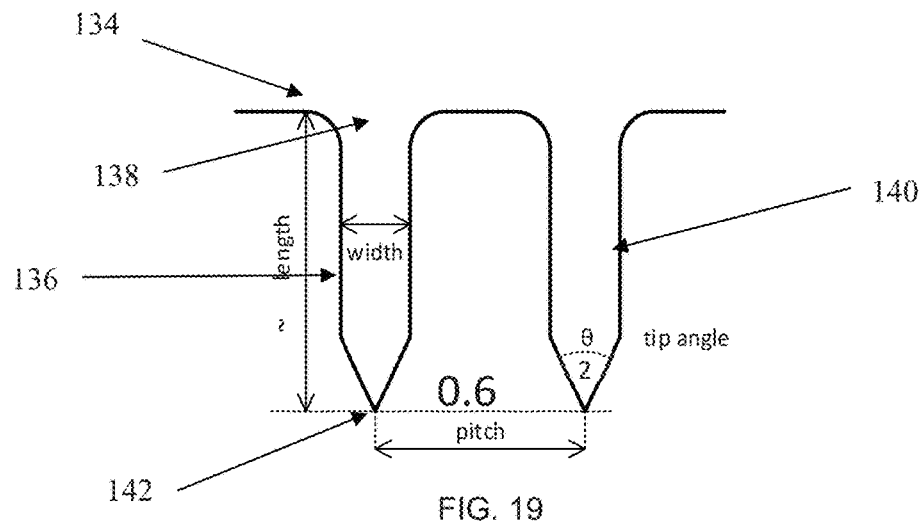
FIG. 19 is a schematic illustration of microprobes of a multi-microprobe sensing microchip according to some embodiments of the present disclosure.

FIG. 14 shows a graph of current (lsd) plotted against working electrode voltage (WE) as the working electrode voltage is swept over a range from −0.7 V to 0.7 V, in some embodiments of the present invention. Each trace represents current levels recorded repeatedly by the same sensor unit as described above. In the sample shown in FIG. 14, current was recorded while the sensors were exposed to phosphate buffer (PB), such that no redox reaction occurred at the working electrode. As a result, the plots of current shown in FIG. 14 follow relatively smooth curves. In a similar experiment, current was recorded while the same sensors were exposed to a 1 mM hydrogen peroxide solution, such that a redox reaction occurred. As a result, a variation in the measured current was induced. As may be seen, an inflection point is present at an equilibrium voltage of about −0.2 V, with maximum current elevation response at about 0.05 V and maximum current elevation response at about −0.45 V. As a result, such a voltage sweep may identify −0.2 V as an inflection point, which is the voltage setting that reduces (e.g., tunes out) a sensor's response to hydrogen peroxide. These findings correlate well with exemplary discrete fixed voltage experiments, the results of which are shown in FIG. 15.

As can be seen in the graph, three different regimes can be observed when the analyte is switched between PB and hydrogen peroxide at different WE potentials. It can be seen from the graph that at a WE voltage of −0.2 v there is negligible net change of the Isd in response to the introduction of hydrogen peroxide, which correlates to the inflection point observed in the voltage sweep experiment (FIG. 15). At a WE voltage of approximately 0-0.1V there is a visible net Isd current elevation in response to hydrogen peroxide which correlates to the maximum current elevation response seen in FIG. 15 at 0.05 v. At a WE voltage of approximately −0.3 v to −0.4 v there is a net Isd current reduction in response to hydrogen peroxide.

Multi-Microprobe Sensing Chip

FIGS. 16-20 depict a multi-microprobe sensing chip 132, according to an exemplary embodiment of the present disclosure. As can be seen in FIGS. 16-19, the sensing chip 132 includes at least one sensing microprobe 136 extending outwardly from a bridge portion 134 of the sensing chip 132. The at least one sensing microprobe 136 has a body 140 that connects a tip of the microprobe 142 to the bridge portion 134. The tip 142 of the microprobe can have any shape, including, without limitation, a conical shape, a cylindrical shape, a tubular shape and a pyramidal shape. In an embodiment, the tip 142 of the at least one microprobe 136 is sharp such that it will form a minimally invasive skin-penetrating microprobe. In some embodiments of the present invention, the at least one microprobe 136 is straight, but non-straight shapes (e.g., a curved microprobe, a hook-shape microprobe, or a semi hook-shape microprobe) are also contemplated. The at least one microprobe 136 can protrude perpendicularly from the bridge portion 134 of the microprobe array. The at least one microprobe 136, in some embodiments of the present invention, has a base 138 attached to or integral with the bridge portion 134 of the sensing chip 132 with the body 140 extending away from the bridge portion 134 of the sensing chip 132. The tip 142 is distal to body 140, which is distal to the base 138.

Figure 20:
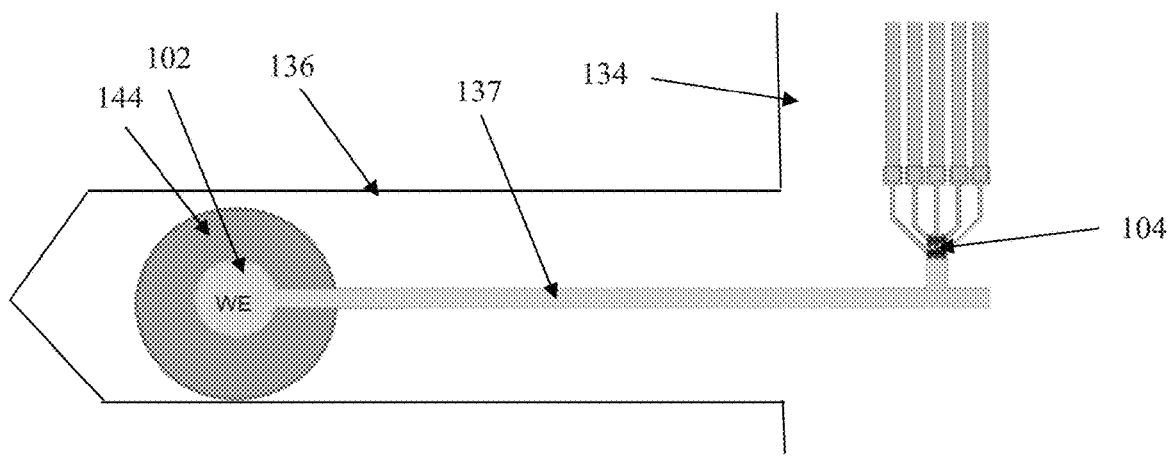
FIG. 20 is a schematic illustration of a SiNW FET sensor setup for a working electrode of a multi-microprobe sensing microchip according to some embodiments of the present disclosure.

The at least one microprobe 136, in some embodiments of the present invention, is hollow or provided with a well 144 embedded therein, and contains at least one opening for allowing the at least one microprobe 136 to exchange fluids with a medium outside the at least one microprobe 136. FIG. 20 is a magnified schematic illustration showing a portion of a sensing microprobe 136 with a well 144 at a distal portion thereof. In another embodiment of the distal well architecture, the FET sensing element can be situated at another environment/compartment such as embedded in a dielectric material which allows the sensing of the WE potential as a result of analyte redox activity at the well portion of the sensor.

The term "well" as used herein refers to a fluid compartment having, in some embodiments, a cross-sectional circular, rectangular, or oval shaped opening. In some embodiments, the opening is oval shaped with a major dimension of less than 0.1 mm, or 0.3 mm, or 0.5 mm, or 0.7 mm, or 0.9 mm, or 1.1 mm, or 1.3 mm, or 1.5 mm. In some embodiments, the oval-shaped opening has a minor dimension that is less than 90%, or 80%, or 70%, or 60%, or 50%, or 40%, or 30%, or 20% of the major dimension.

In some embodiments, the opening is substantially rectangular shaped with a major dimension of less than 0.1 mm, 0.3 mm, 0.5 mm, 0.7 mm, 0.9 mm, 1.1 mm, 1.3 mm or 1.5 mm. In some embodiments, the substantially rectangular opening has a minor dimension of less than 90%, or 80%, or 70%, or 60%, or 50%, or 40%, or 30% or 20% of the major dimension.

In some embodiments of the present invention, the at least one microprobe has an opening at the tip. In some embodiments of the present invention, the at least one microprobe or a portion thereof can be porous. Alternatively, the at least one microprobe can be non-porous with only one or a few openings formed on its body. The at least one microprobe, in some embodiments of the present invention, comprises a non-degradable material.

In some embodiments of the present invention, the diameter of the at least one microprobe is selected to leave a residual hole (following microprobe insertion and withdrawal) of less than about 1 µm, to avoid making a hole which would allow bacteria to enter the penetration wound. The length of the penetrating portion is, in some embodiments of the present invention, selected to allow the penetrating portion to penetrate the skin, for example, beyond the stratum corneum layer. In some embodiments of the present invention, the length of the penetrating portion is selected to positioning tip in the viable epidermal layer but not in the dermal layer. In exemplary embodiments, the length of the penetrating portion is from 0.05 mm to 1 mm, or from 0.05 to 0.8 mm, or from 0.5 mm to 0.75 mm, or from 0.05 mm to 0.6 mm, or from 0.05 mm to 0.5 mm, or from 0.05 mm to 0.4 mm, or 0.05 mm to 0.3 mm, or from 0.05 mm to 0.25 mm, or from 0.05 mm to 0.15 mm.

In some embodiments of the present invention, the length of the penetrating portion is from 0.05 mm to 1 mm, or from 0.15 mm to 1 mm, or from 0.2 mm to 1 mm, or from 0.35 mm to 1 mm, or from 0.45 mm to 1 mm, or from 0.5 mm to 1 mm, or from 0.75 mm to 1 mm, or from 0.85 mm to 1 mm, or from 0.9 mm to 1 mm.

In some embodiments of the present invention, the length of the penetrating portion is from 0.35 mm to 0.75 mm, or from 0.55 mm to 0.65 mm, or from 0.75 mm to 0.95 mm. In other embodiments, the length of the penetrating portion is less than 1 mm, or less than 2 mm, or less than 3 mm, or less than 4 mm, or less than 5 mm.

The sensing chip can be constructed from any of a variety of materials including, without limitations, metals, ceramics, semiconductors, organics, polymers and composites.

In some embodiments of the present invention, the microprobe array includes microprobes of various lengths, base portion materials, body portion diameters (i.e. gauge), tip portion shapes, spacing between microprobes, coatings, etc.

In some embodiments of the present invention, each microprobe 136 includes a FET sensor 100 positioned at, but not limited to the distal portion of the microprobe 136. A magnified schematic illustration of the FET sensor 100 positioned on the at least one microprobe 136 according to some embodiments of the present invention is shown in FIG. 20. As depicted in the figure, each microprobe 136 includes a working electrode 102 that is positioned at the well 144 so as to be in contact with the analyte solution 120 that collects within it, when the microprobe 136 is immersed in an analyte. The working electrode 102 includes a trace 137 that extends at least a portion of the length of the at least one microprobe 136 to the main portion 134 of the sensing chip 132. In some embodiments, the working electrode 102 and the trace 137 are formed of the same material. In some embodiments, a portion of the working electrode 102 and/or the trace 137 may be covered or encapsulated. As shown in FIG. 20, on the main portion 134 of the sensing chip 132, at least one FET amplifier 104 is positioned in close proximity to the working electrode 102. As described above, the FET amplifier 104 includes a source terminal 106, a drain terminal 108, and at least one nanowire 110 connecting the source and drain terminals 106, 108. In exemplary embodiments, each FET sensor 100 is designed to be functionalized using different analyte-specific materials, such as a sensing hydrogel 116 embedded with enzymes described above, in order to achieve multi-metabolite sensing capabilities. For example, in some embodiments of the present invention, each FET sensor may comprise a sensing hydrogel 116 attached to the working electrode 102 embedded in the at least one microprobe 136.

In some embodiments, the at least one microprobe 136 may each include two FET sensors 100. In some embodiments of the present invention, the FET sensor 100 includes more than one FET amplifier 104 detecting the electrical change in the working electrode 102.

In some embodiments of the present invention, the chip includes one or more microprobes used for calibration, which are also outwardly protruding from the main portion, similar to the at least one sensing microprobe. Calibration microprobes may have the same structure as the at least one sensing microprobe but are, in some embodiments of the present invention, devoid of a hydrogel containing an enzyme or any moiety configured to react with analytes in the analyte solution. However, in some embodiments of the present invention, the calibration microprobes include hydrogels with moieties having an affinity to a substance other than a bioanalyte. Alternatively, the calibration microprobes may have hydrogels with non-sensing moieties or enzymes.

Figure 21:
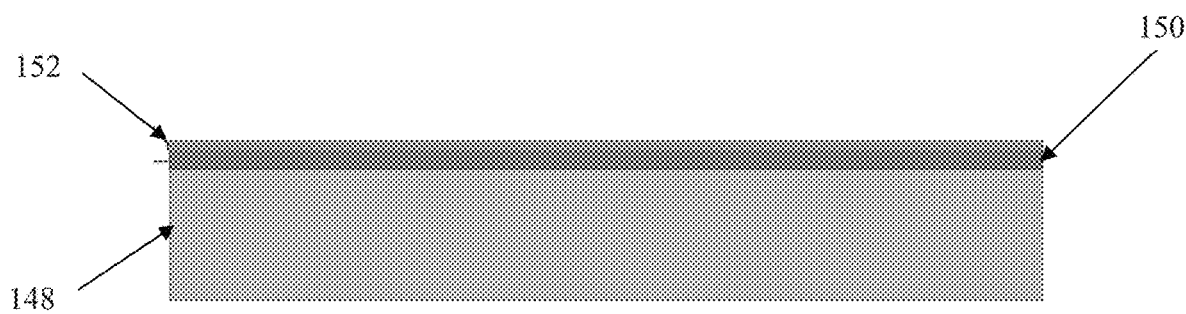
FIG. 21 is a schematic illustration of a silicon-on-insulator wafer prior to production of a multi-microprobe sensing microchip, according to some embodiments of the present disclosure.

FIGS. 21-32 illustrate an exemplary method of microchip production, in some embodiments of the present invention. As depicted in FIG. 21, in an exemplary embodiment, a silicon-on-insulator (SOI) wafer 148 with a buried oxide layer 150 and an ultrathin silicon device layer (for example, <100 nm) 152 is used. The device layer may have, for example, a dopant concentration of $10^{15}$-$10^{17}$ atoms/cm$^3$.

Figure 22:
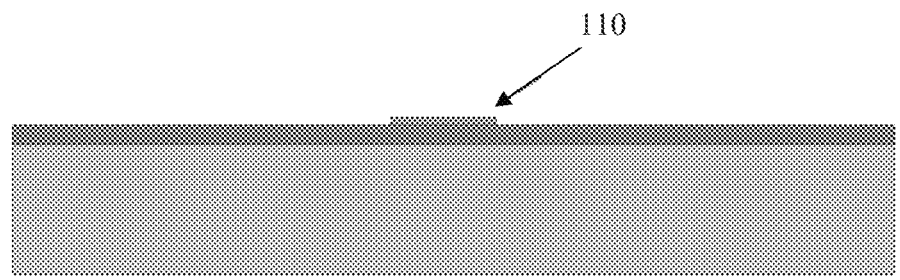
FIG. 22 is a schematic illustration of a first step in an exemplary method of production of a multi-microprobe sensing microchip, according to some embodiments of the present disclosure.

In step 1, as depicted in FIG. 22, the silicon device layer 152 is lithographically patterned via e-Beam, stepper or scanner lithography or other equivalent nano-lithography techniques. The device layer 152 may then be etched via wet anisotropic chemical etching or dry, plasma-based silicon etching with reactive species to form the at least one nanowire 110 or nanowire arrays.

Figure 23:
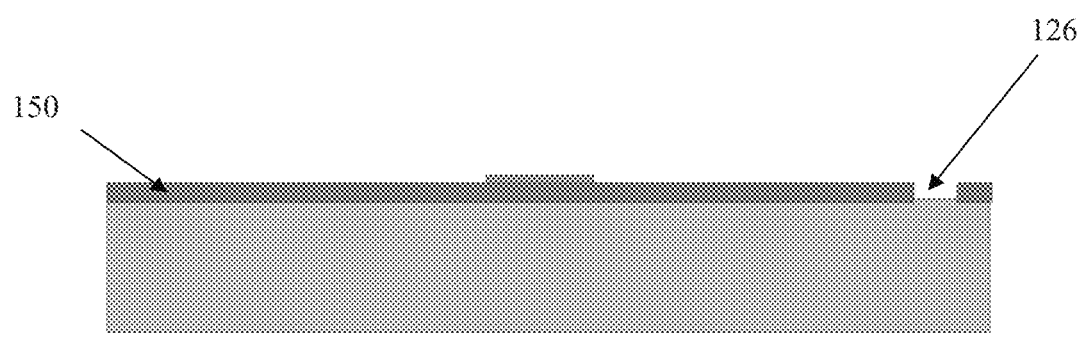
FIG. 23 is a schematic illustration of a second step in an exemplary method of production of a multi-microprobe sensing microchip, according to some embodiments of the present disclosure.

In step 2, after the at least one nanowire 110 is formed, the back gate 126 is etched, through the buried oxide layer 150, as shown in FIG. 23. Specifically, the back gate 126 is lithographically patterned and then etched through the buried oxide layer 150 via photolithography, stepper or scanner lithography. The buried oxide layer 150 is then etched via wet isotropic chemical etching or dry, plasma based silicon dioxide etching with a reactive species.

Figure 24:
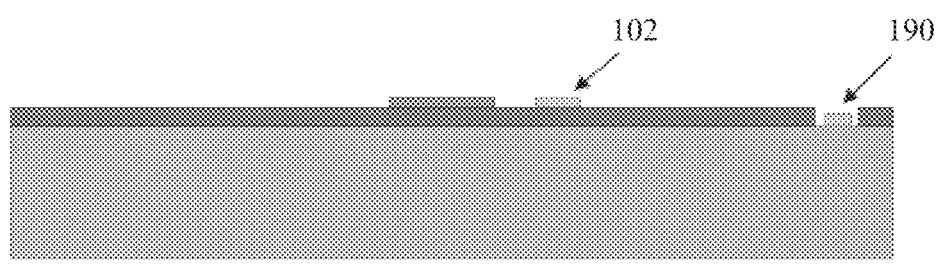
FIG. 24 is a schematic illustration of a third step in an exemplary method of production of a multi-microprobe sensing microchip, according to some embodiments of the present disclosure.

In step 3, depicted in FIG. 24, photolithography, stepper or scanner lithography is used to lithographically pattern resist for the working electrode 102 and bond pads 190. Specifically, a metal stack is deposited in the lithographically patterned resist via evaporation, sputtering or electrodeposition. The metal stack includes an initial layer for adhesion and silicide formation as well as a noble metal layer for exposure to environment. In some embodiments of the present invention, the initial layer is one of Titanium, Nickel or TiN.

Figure 25:
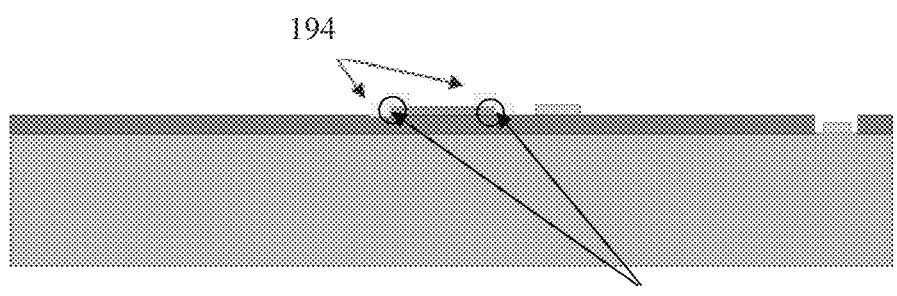
FIG. 25 is a schematic illustration of a fourth step in an exemplary method of production of a multi-microprobe sensing microchip, according to some embodiments of the present disclosure.

In step 4, depicted in FIG. 25, native silicon dioxide is etched via wet isotropic etching or dry etching and a metal stack 194 is deposited in a lithographically patterned resist via evaporation, sputtering or electrodeposition to form the nanowire contacts 196 between the metal stack and the nanowire, in this embodiment, the SiNW 110. In some embodiments, the metal stack 194 includes an initial layer for adhesion and silicide formation (Ti, Ni or TiN) a second metal layer with lower electrical resistance (Al, AlSi, AlSiCu, Pd, Au, Cu or Ag) and a third top layer (Ti, Al, Cr) for improved adhesion to following passivation layers.

Figure 26:
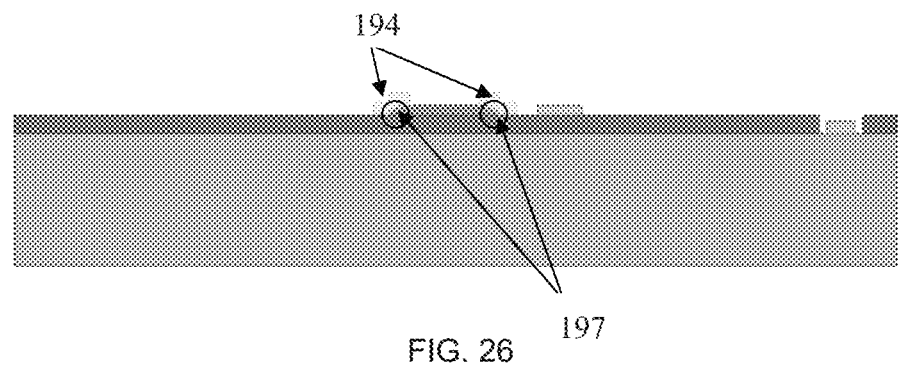
FIG. 26 is a schematic illustration of a fifth step in an exemplary method of production of a multi-microprobe sensing microchip, according to some embodiments of the present disclosure.

In step 5, depicted in FIG. 26, the at least one nanowire contact (not shown) may undergo rapid thermal annealing (RTA) in an inert nitrogen or argon atmosphere or with forming gas. The RTA-induced silicide formation results in a transformation of the nanowire contact into an interface volume 197.

Figure 27:
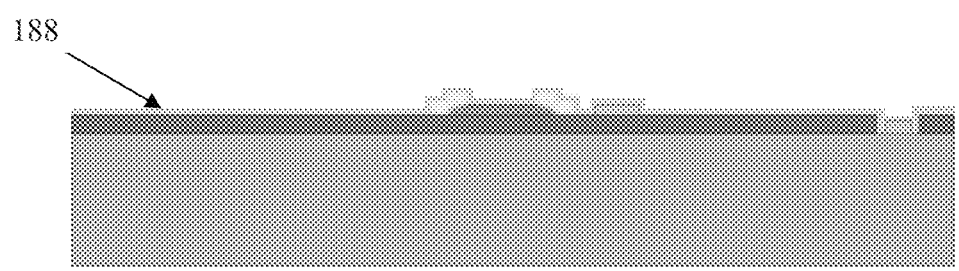
FIG. 27 is a schematic illustration of a sixth step in an exemplary method of production of a mufti-microprobe sensing microchip, according to some embodiments of the present disclosure.

In step 6, depicted in FIG. 27, a passivation layer 188 is deposited for electrical isolation via atomic layer deposition (ALD), inductively coupled plasma-chemical vapor deposition (JCP-CVD) or Tetraethylorthosilicate (TEOS), The passivation layer 188, in some embodiments of the present invention, comprises one of aluminum oxide, silicon nitride, silicon dioxide or silicon oxynitride.

Figure 28:
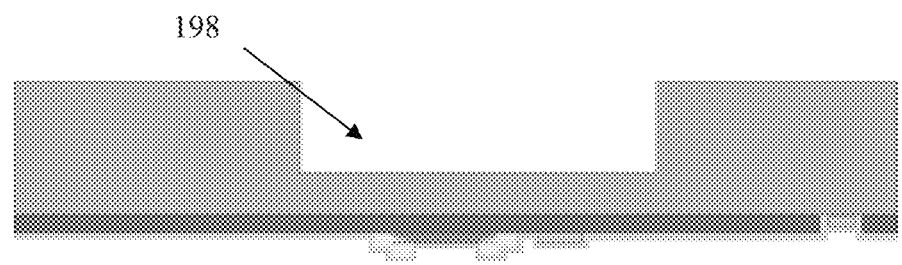
FIG. 28 is a schematic illustration of a seventh step in an exemplary method of production of a multi-microprobe sensing microchip, according to some embodiments of the present disclosure.

In step 7, depicted in FIG. 28, a resist is lithographically patterned in the back of the wafer via photolithography, stepper or scanner lithography. A back gate handle 198 is etched with silicon via wet anisotropic silicon etching or plasma based anisotropic deep silicon etching (DSE).

Figure 29:
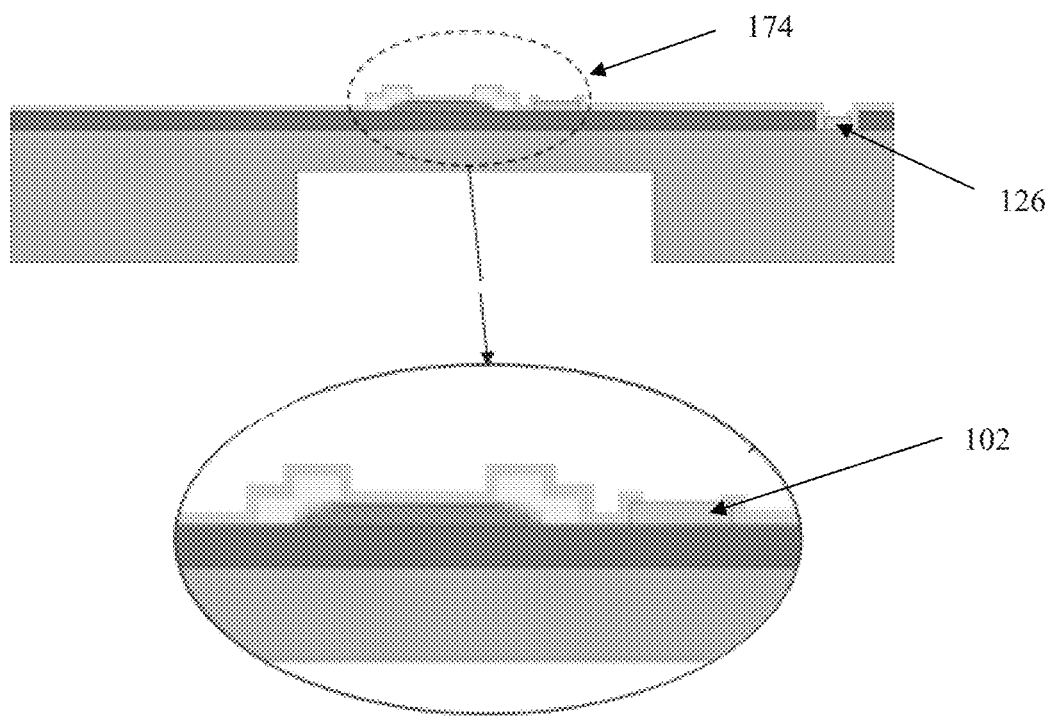
FIG. 29 is a schematic illustration of an eighth step in an exemplary method of production of a multi-microprobe sensing microchip, according to some embodiments of the present disclosure.
Figure 30:
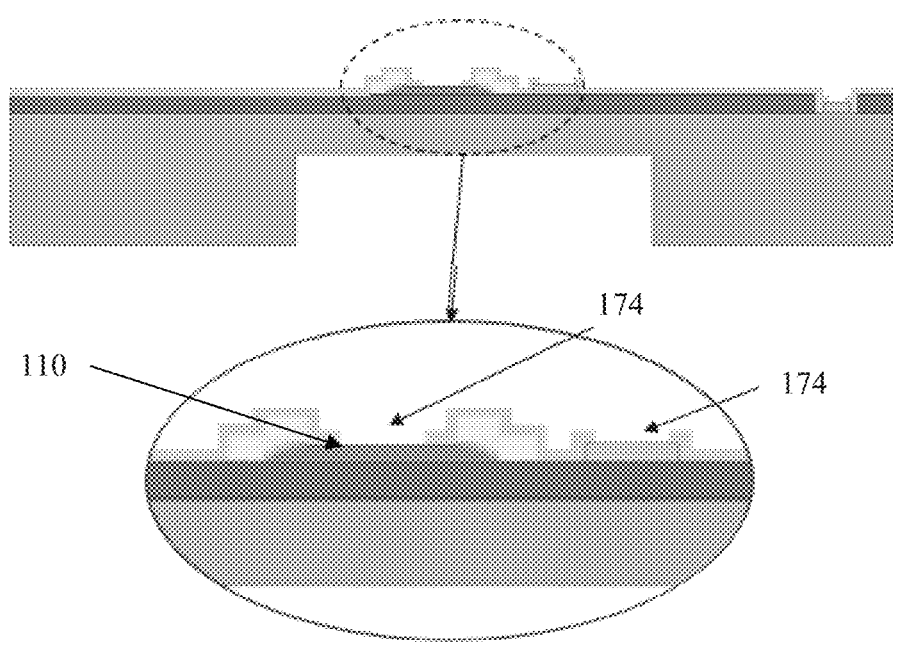
FIG. 30 is a schematic illustration of a ninth step in an exemplary method of production of a multi-microprobe sensing microchip, according to some embodiments of the present disclosure.

In step 8, depicted in FIGS. 29-30, openings 174 are lithographically patterned on the passivation layer 188. The openings 174 are then etched through the passivation layer 188 via isotropic wet chemical etching or plasma based dry etching with a reactive species to expose the working electrode 102, the back gate electrode 126 and the at least one nanowire 110. This etching exposes the noble metal of the at least one nanowire 110 to the environment.

Figure 31:
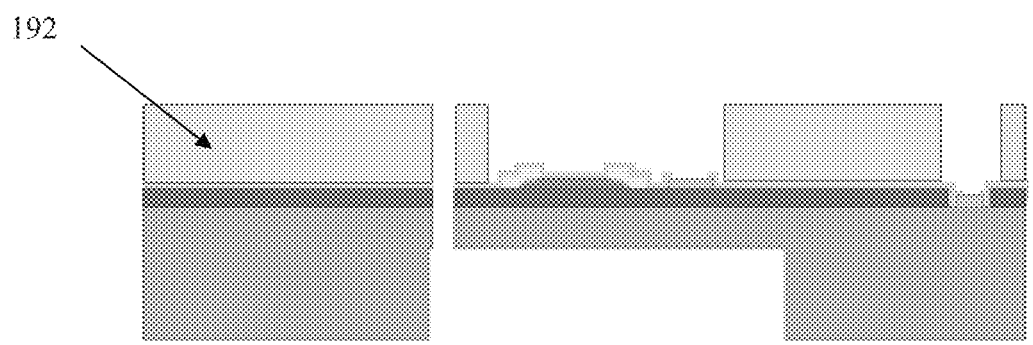
FIG. 31 is a schematic illustration of a tenth step in an exemplary method of production of a multi-microprobe sensing microchip, according to some embodiments of the present disclosure.

In step 9, depicted in FIG. 31, a thick, permanent photoresist 192 is lithographically patterned via photolithography, stepper or scanner lithography to form the well 144. In some embodiments of the present invention, the photoresist 192 is in the range of 5 to 50 microns. In some embodiments of the present invention, the photoresist 192 is formed of SU-8 or polyimide.

In step 10, depicted in FIG. 31, a resist is lithographically patterned via photolithography, stepper or scanner lithography to define a well 144 and well walls 143 the at least one microprobe and the microchip. The passivation layer is then etched via wet chemical etching or plasma based dry etching with a reactive species. The buried oxide layer is also etched with wet chemical etching or plasma based dry etching with reactive species while the handle layer silicon is etched via plasma based anisotropic deep silicon etching (DSE).

Figure 32:
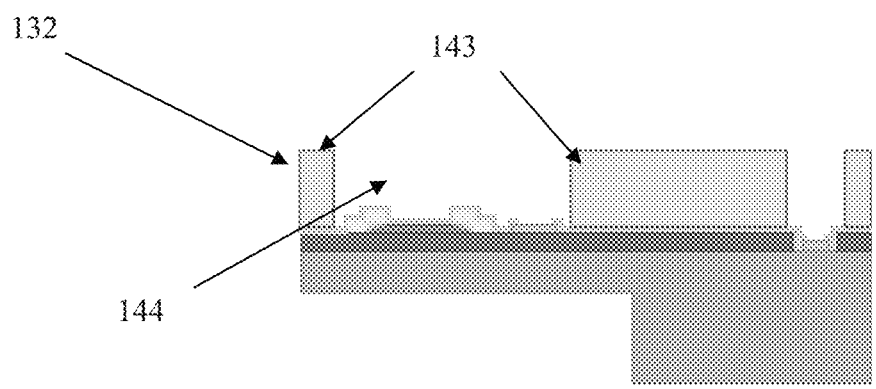
FIG. 32 is a schematic illustration of an eleventh step in an exemplary method of production of a multi-microprobe sensing microchip, according to some embodiments of the present disclosure.

Finally, in step 11, depicted in FIG. 32, the singulated microchip 132 is removed from the silicon wafer by breaking tabs connecting the microchip 132 to the wafer.

Figure 33:
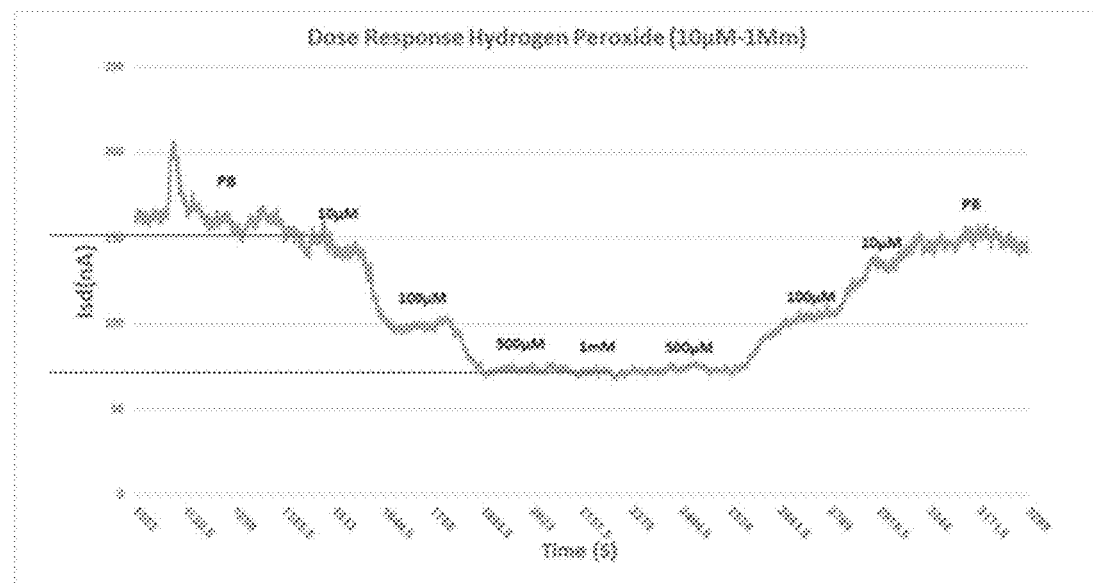
FIG. 33 is a graph depicting current flow from a SiNW FET sensor over time, according to some embodiments of the present disclosure.

FIG. 33 depicts how, in use, a microchip 132 with a single FET sensor 100 can measure different concentrations of, for example, a chemical species over time, in some embodiments of the present invention. In this embodiment, the FET sensor 100 is tuned to measure hydrogen peroxide. FIG. 33 shows the recording of current flow from the single FET sensor 100 over time. The measurement was done under a fixed working electrode voltage. As can be seen from the graph, changing the hydrogen peroxide concentration results in a change of the current levels through the FET amplifier 104. Specifically, an increase in hydrogen peroxide concentration results in a reduction of the current level while a decrease in the hydrogen peroxide concentration results in an increase in the current level. For example, changing the hydrogen peroxide concentration from 10 μM to 1 mM reduces the current level from approximately 150 nA to 70 nA.

Figure 34:
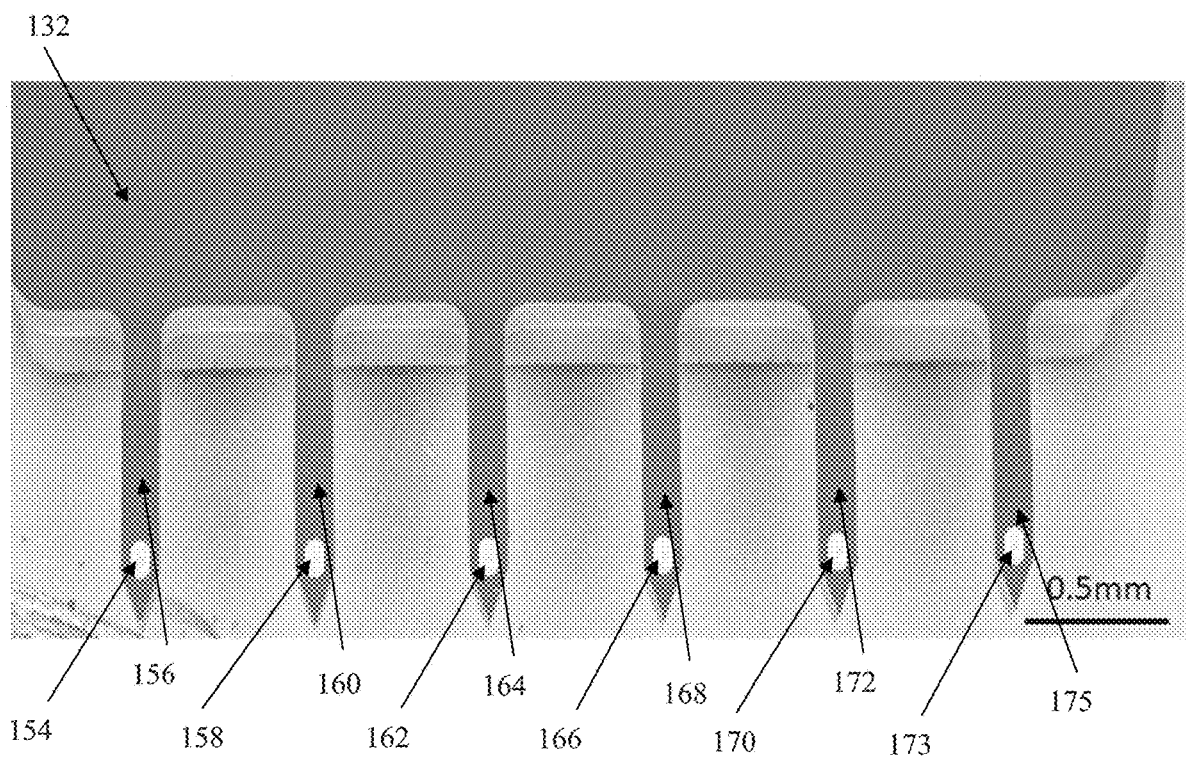
FIG. 34 is a magnified view of a multi-microprobe sensing chip according to some embodiments of the present disclosure.

FIG. 34 depicts an exemplary setup of a multi-microprobe sensing chip 132 configured for monitoring, in this example, glucose, lactate and ascorbic acid (AA) in an analyte solution, in some embodiments of the present invention. In this embodiment, the multi-microprobe sensing chip includes six microprobes, each including an FET sensor. The exemplary embodiments include a specific discussion of devices configured to detect glucose, lactate and ascorbic acid, but it will be apparent to those of skill in the art that devices can be configured to detect other analytes (i.e., β-d-Glucose, L-lactate, Glutamine, cholesterol, Glycerol, pyruvate, Ethanol L-glutamate, Choline Acetylcholine, I-Ascorbic acid, cortisol, Creatine, Creatinine, 2-hydroxybutyrate or 3-hydroxybutyrate) through the use of enzymes (i.e., glucose oxidase, lactate oxidase, cholesterol oxidase, pyruvate oxidase, Glycerol oxidase, Alcohol oxidase, Glutaminase oxidase, L-glutamate oxidase, Xanthine oxidase, L-glutamate oxidase, Choline oxidase, Sarcosine oxidase and Ascorbate oxidase or creatininase, Creatinase, Peroxidase, Laccase, Tyrosinase or 3-hydroxybutyrate dehydrogenase, Glucose dehydrogenase, Lactate dehydrogenase, Alcohol dehydrogenase, Glutamate dehydroge) for such other analytes as enzyme substrates without departing from the broader principles described herein.

Specifically, the multi-microprobe sensing microchip 132 includes a first microprobe 154 having a first FET sensor 156. The working electrode of the first FET sensor 156, in this embodiment, is embedded with a GOX-containing hydrogel. The GOX reacts with glucose in the analyte solution to produce hydrogen peroxide ($H_2O_2$). A second microprobe 158 of the microchip 132 includes a second FET sensor 160. A working electrode of the second FET sensor 160, in this embodiment, is embedded with a LOX-containing hydrogel. The LOX reacts with lactate in the analyte solution to produce $H_2O_2$. A third microprobe 162 of the multi-microprobe sensing chip 132 includes a third FET sensor 164. However, the working electrode of the third FET sensor 164 is embedded with a hydrogel devoid of any enzymes. Thus, the third FET sensor 164 detects all background analytes within the analyte solution to allow for correction of the measurements from the first and second FET sensors 156, 160. In this embodiment, each of the first, second and third FET sensors 156, 160, 164 have the same voltage setting so that the third FET sensor 164 acts as a blank sensor to compensate for background noise. Thus, by deducting the third FET sensor output from the first FET sensor output, amounts of glucose within the analyte solution can be calculated. Similarly, by deducting the third FET sensor output from the second FET sensor output, amounts of lactate within the analyte solution can be calculated.

Turning to the fourth microprobe 166 of the multi-microprobe sensing chip 132, a fourth FET sensor 168 positioned thereon is designated, in this embodiment as an ascorbic acid sensor. The working electrode of the fourth FET sensor 166, in this embodiment, is embedded with a hydrogel that is devoid of enzymes, while its voltage is tuned to maximize ascorbic acid (AA) sensing. For example, the back gate/working electrode voltage may be set to more negative values. A fifth microprobe 170 of the multi-microprobe sensing chip 132 includes a fifth FET sensor 172. The working electrode of the fifth FET sensor 172, in this embodiment, is embedded with ascorbic acid oxidase (AAOX), which does not produce hydrogen peroxide, only dehydroascorbic acid and water. Thus, the AAOX is used to eliminate AA and by deducting the fifth FET sensor output from the fourth sensor output, AA concentration can be calculated. A sixth microprobe 173 of the multi-needle sensing chip 132 includes a sixth FET sensor 175. The working electrode of the sixth FET sensor 175, in this embodiment, is embedded with an ion-specific ionophore membrane to allow the measurement of specific ion such as Beauvericin (Ca2+, Ba2+), Calcimycine or A23187 (Mn2+, Ca2+, Mg2+), Cezomycin, Carbonyl cyanide m-chlorophenyl hydrazone (CCCP) (H+), Enniatin (ammonium), ramicidin A (H+, Na+, K+), Ionomycin (Ca2+), Lasalocid (K+, Na+, Ca2+, Mg2+), Monensin (Na+, H+), Nigericin (K+, H+, Pb2+), Nonactin (ammonium ionophore I), Salinomycin (K+), Tetronasin, Valinomycin (potassium ionophore I), Narasin, or combinations thereof.

Microprobe Sensing System

Figure 35:
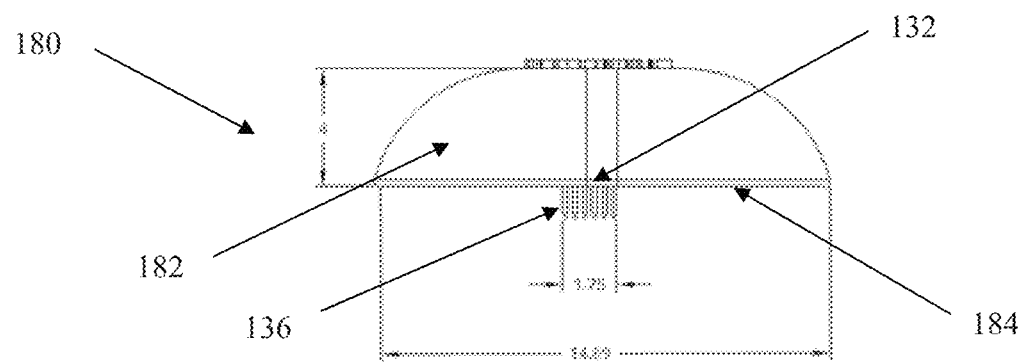
FIG. 35 is a schematic illustration of a microprobe sensing system according to some embodiments of the present disclosure.
Figure 36:
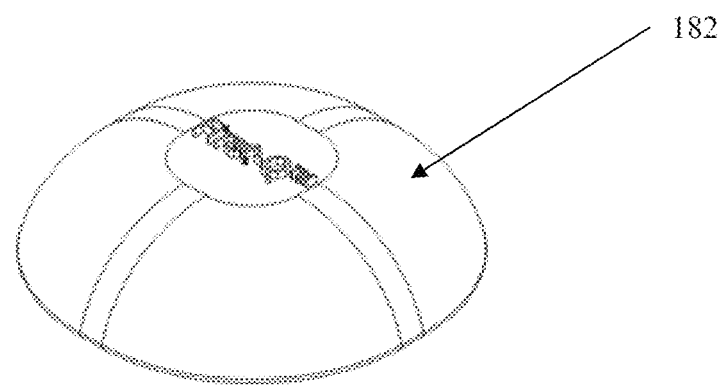
FIG. 36 is a perspective view of a patch portion of a microprobe sensing system according to some embodiments of the present disclosure.

In some embodiments of the present invention, depicted in FIGS. 35-36, the multi-microprobe sensing chip 132 is incorporated into a sensing system 180. The sensing system 180, in some embodiments of the present invention, is configured as a patch or removable implant that allows for monitoring presence, absence or amounts of multiple bioanalytes. As depicted in FIG. 35, in some embodiments of the present invention, the sensing system 180 comprises a sensor patch 182 having a skin contact surface 184 for contacting the skin of a subject (human or animal). The sensor patch 182, in some embodiments of the present invention, is configured to hold the multi-microprobe sensing chip 132 such that one or more sensing microprobes 136 outwardly protrude from the skin contacting surface. In exemplary embodiments, the at least one microprobe 136 can protrude perpendicularly from the surface 184 of the sensor patch 182, or at an acute angle from the surface 184. In some embodiments of the present invention, a circuit is attached to the sensor patch 182. In some embodiments of the present invention, the circuit is positioned at an opposite side of the substrate relative to the microprobes.

FIG. 36 depicts a sensor patch 182, according to an exemplary embodiment of the present disclosure. The sensor patch surface 184 is, in some embodiments of the present invention, an adherent surface, allowing the substrate to be attached to the skin. For example, the surface can comprise, or be coated with, a skin adherent material. In some embodiments of the present invention, the sensor patch 182 also contains a substance selected for preventing or reducing skin irritations such as, but not limited to, pruritus, flush, rash, pain, eczema and skin inflammation. In some embodiments of the present invention, the sensor patch 182 is flexible. For example, the sensor patch 182 can be made, at least in part, of a woven fabric, a nonwoven fabric, a plastic film or the like. Portions of the sensor patch 182 are made, for example, of elastomeric polymer. Suitable elastomeric polymer substrate materials are generally selected based upon their compatibility with the manufacturing process (soft lithography, stereo lithography and three-dimensional jet printing, etc.). Given the tremendous diversity of polymer chemistries, precursors, synthetic methods, reaction conditions, and potential additives, there is a large number of materials that are contemplated for use. Representative examples of elastomeric polymers include, without limitation, polydimethylsiloxane (PDMS), polyisoprene, polybutadiene, polychloroprene, polyisobutylene, polystyrene-butadiene-styrene), polyurethanes and silicones. Polymers which are generally non-elastomeric are also contemplated. Representative examples of such polymers include, without limitation, PMMA and polycarbonate.

Also contemplated are embodiments in which the sensor patch 182 is made of two or more materials. For example, a portion of the sensor patch 182 can be made from a woven or nonwoven fabric, or film, that is, in some embodiments of the present invention, coated with a skin adherent material, while another portion serves as a microfluidic interface, wherein microprobes 136, are formed on or integral with microfluidic interface. Microfluidic interface can be made more rigid than the fabric or film.

The lateral dimensions of sensor patch 182 may vary, depending on the size of the organ of the subject that receives surface 14. A typical lateral diameter of sensor patch 182 is, without limitation, from about 10 mm to about 50 mm.

As noted above, in some embodiments of the present invention, the FET sensor response to a redox species in an analyte solution can be processed and measured by, for example, the circuit. In some embodiments of the present invention, the circuit can be constructed, for example, to measure the current passing through the drain terminal of the FET amplifier.

The FET amplifiers positioned on the sensing chip are, in some embodiments of the present invention, connected directly or indirectly to the circuit. The circuit applies voltage to the FET amplifier. The circuit typically includes a power source and a voltmeter or amperemeter. When the reaction between the sensing hydrogel and the analytes in solution is a redox reaction, the circuit, in some embodiments of the present invention, is configured for controlling the voltage settings of the back gate to the working electrode.

It is appreciated that certain features of the disclosure, which are, for clarity, described in the context of separate embodiments, may also be provided in a single embodiment. Conversely, various features of the disclosure, which are, for brevity, described in the context of a single embodiment, may also be provided separately or in any suitable sub combination or as suitable in any other described embodiment of the disclosure. Certain features described in the context of various embodiments are not considered essential features of these embodiments, unless the embodiment is inoperative without those elements.

What is claimed is:

1. A microprobe sensing device, comprising:
   a plurality of microprobes, each microprobe including a tip configured to be inserted into an analyte solution and a sensor positioned at the tip, wherein each sensor comprises:
   a working electrode configured to be positioned in contact with the analyte solution,
   a voltage source coupled to the working electrode,
   an amplifier comprising:
      a source terminal,
      a drain terminal, and
      a plurality of nanowires,
         wherein each of the plurality of nanowires electrically connects the source terminal to the drain terminal,
         wherein each of the plurality of nanowires has a major cross section dimension in the range of 1 to 500 nanometers,
   a back gate electrode,
   a dielectric layer positioned between the back gate electrode and the amplifier, and
   an insulator having a first side and a second side opposite the first side,
      wherein the working electrode is positioned to the first side of the insulator, and
      wherein (a) the source terminal, (b) the drain terminal, and (c) the plurality of nanowires are positioned to the second side of the insulator,
      whereby the insulator is configured to prevent direct electrical contact between the working electrode and either (a) the source terminal, (b) the drain terminal, or (c) the plurality of nanowires, and
      whereby the insulator is configured to prevent direct contact between the analyte solution and either (a) the source terminal, (b) the drain terminal, or (c) the plurality of nanowires,
   wherein the sensor is configured such that only the working electrode contacts the analyte solution, which is through an exposed part,
   wherein the working electrode is configured such that, when a chemical species is present in the analyte solution, a variation in an electrical field at a location of the plurality of nanowires is induced, and
   wherein the plurality of nanowires is configured such that, when the electrical field varies, a corresponding variation in an electrical current between the source terminal and the drain terminal is induced.

2. The microprobe sensing device of claim 1, wherein a distance between the source terminal and the drain terminal is in a range of 0.5 microns to 10 microns.

3. The microprobe sensing device of claim 1, wherein a distance between the source terminal and the drain terminal is in a range of 10 microns to 100 microns.

4. The microprobe sensing device of claim 1, wherein the insulator has a thickness in a range of 10 nanometers to 1 micron.

5. The microprobe sensing device of claim 1, wherein the working electrode comprises at least one of a noble metal or a metal oxide.

6. The microprobe sensing device of claim 1, wherein the sensor has a footprint that is in a range of from 0.00005 $mm^2$ to 0.005 $mm^2$.

7. The microprobe sensing device of claim 1, wherein an exposed part of the working electrode has a major dimension that is in a range of from 1 micron to 1,000 microns.

8. The device of claim 1, wherein a first one of the plurality of microprobes is configured to detect a first analyte, and wherein a second one of the plurality of microprobes is configured to detect a second analyte that is different from the first analyte.

9. The device of claim 1, wherein at least one of the plurality of microprobes is a nonspecific sensor.

10. The device of claim 1, wherein the plurality of microprobes is positioned in parallel.

11. The device of claim 1, wherein a first one of the plurality of microprobes is configured to detect a first analyte, and wherein a second one of the plurality of microprobes is configured to detect the first analyte.

12. The device of claim 11, wherein the first one of the plurality of microprobes and the second one of the plurality of microprobes are configured to detect the first analyte with a different specificity from one another.

13. The device of claim 12, wherein the first one of the plurality of microprobes and the second one of the plurality of microprobes have different analyte-specific curves from one another.

14. The device of claim 12, wherein the second one of the plurality of microprobes comprises a limiting membrane to control sensitivity to the first analyte.

15. A method of determining the amount of an analyte in an analyte solution containing the analyte, the method comprising:
   inserting a tip of a first microprobe and a tip of a second microprobe of a sensing device into the analyte solution, wherein each of the first and second microprobes includes a sensor positioned at the tip, wherein each sensor comprises:
a working electrode configured to be positioned in contact with an analyte solution;
a voltage source coupled to the working electrode;
an amplifier, comprising:
a source terminal;
a drain terminal; and
a plurality of nanowires,
wherein each of the nanowires electrically connects the source terminal to the drain terminal;
a back gate electrode,
a dielectric layer positioned between the back gate electrode and the field-effect transistor amplifier, and
an insulator having a first side and a second side opposite the first side,
wherein the working electrode is positioned to the first side of the insulator,
wherein (a) the source terminal, (b) the drain terminal, and (c) the plurality of nanowires are positioned to the second side of the insulator,
whereby the insulator is configured to prevent direct electrical contact between the working electrode and either (a) the source terminal, (b) the drain terminal, or (c) the plurality of nanowires, and
whereby the insulator is configured to prevent direct contact between the analyte solution and either (a) the source terminal, (b) the drain terminal, or (c) the plurality of nanowires,
wherein the working electrode of the sensor of each of the first and second microprobes includes a hydrogel embedded therein,
wherein the hydrogel of the first microprobe contains an enzyme configured to interact with the analyte;
inducing a first variation in a first electrical field at a location of the plurality of nanowires of the sensor of the first microprobe by a reaction of the enzyme with the analyte in the analyte solution to thereby create a shift in the potential at the working electrode of the sensor of the first microprobe;
inducing a second variation in a second electrical field at a location of the plurality of nanowires of the sensor of the second microprobe by redox interaction of the working electrode of the sensor of the second microprobe with the redox species present in the analyte solution;
inducing a first variation in a first electrical current between the source terminal of the sensor of the first microprobe and the drain terminal of the sensor of the first microprobe, the first variation in the first electrical current corresponding to the first variation of the first electrical field;
inducing a second variation in a second electrical current between the source terminal of the sensor of the second microprobe and the drain terminal of the sensor of the second microprobe, the second variation in the second electrical current corresponding to the second variation of the second electrical field; and
determining an amount of the analyte present in the analyte solution based on a difference between the first variation in the first electrical current and the second variation in the second electrical current.

16. The method of claim 15, wherein the inducing a first variation in a first electrical field at a location of the plurality of nanowires of the sensor of the first microprobe by a reaction of the enzyme with the analyte in the analyte solution to thereby create a shift in the potential at the working electrode of the sensor of the first microprobe comprises:
(a) a reaction of the enzyme with the analyte in the analyte solution to thereby produce an electron transport mediator; and
(b) a redox interaction of the working electrode of the sensor of the first microprobe with:
(1) a redox species present in the analyte solution, and
(2) the electron transport mediator formed by the reaction of the enzyme with the analyte.

17. The method of claim 16, wherein the electron transport mediator is one of hydrogen peroxide, nicotinamide adenine dinucleotide (NADH), ascorbic acid, caffeine, acetaminophen, flavin adenine dinucleotide (FAD), flavin mononucleotide (FMN), or quinone cofactors.

18. The method of claim 15, wherein the enzyme includes one of glucose oxidase, lactate oxidase, 3-hydroxybutyrate dehydrogenase, cholesterol oxidase, pyruvate oxidase, glycerol oxidase, alcohol oxidase, glutaminase oxidase, L-glutamate oxidase, xanthine oxidase, L-glutamate oxidase, choline oxidase, sarcosine oxidase, ascorbate oxidase, creatininase, creatinase, peroxidase, laccase, tyrosinase, 3-hydroxybutyrate dehydrogenase, glucose dehydrogenase, Lactate lactate dehydrogenase, alcohol dehydrogenase, or glutamate dehydrogenase.

19. The method of claim 15, wherein the hydrogel is configured to interact with at least one of β-d-glucose, L-lactate, glutamine, cholesterol, glycerol, pyruvate, ethanol L-glutamate, choline acetylcholine, L-ascorbic acid, cortisol, creatine, creatinine, 2-hydroxybutyrate, or 3-hydroxybutyrate.

20. The method of claim 15, wherein each sensor further comprises an adhesive layer deposited on the working electrode, the adhesive layer configured to adhere the hydrogel to the working electrode.

21. A method for calibrating a sensor, the method comprising:
inserting a sensor positioned at a tip of a sensing device into an analyte solution, the sensor comprising:
a working electrode configured to be positioned in contact with an analyte solution;
a voltage source coupled to the working electrode;
an amplifier, comprising:
a source terminal;
a drain terminal; and
a plurality of nanowires,
wherein each of the plurality of nanowires electrically connects the source terminal to the drain terminal;
a back gate electrode,
a dielectric layer positioned between the back gate electrode and the amplifier, and
an insulator having a first side and a second side opposite the first side,
wherein the working electrode is positioned to the first side of the insulator, wherein (a) the source terminal, (b) the drain terminal, and (c) the plurality of nanowires are positioned to the second side of the insulator,
whereby the insulator is configured to prevent direct electrical contact between the working electrode and either (a) the source terminal, (b) the drain terminal, or (c) the plurality of nanowires, and
whereby the insulator is configured to prevent direct contact between the analyte solution and either (a)

the source terminal, (b) the drain terminal, or (c) the plurality of nanowires,
wherein the working electrode is configured such that, when an chemical species are present in the analyte solution, a variation in an electrical field at a location of the plurality of nanowires is induced,
wherein the plurality of nanowires is configured such that, when the electrical field varies, a corresponding variation in an electrical current between the source terminal and the drain terminal is induced,
identifying a singularity point in a performance graph of a sensor for a given analyte by adjusting (a) a back gate voltage (b) a working electrode voltage and (c) a source voltage, such that a maximum variation in an electrical current between the source terminal and the drain terminal is induced by the presence of the analyte,
wherein the performance graph of the sensor comprises a graph of source-drain current with respect to working electrode voltage, and
wherein the singularity point is a point in the performance graph that comprises a value of the working electrode voltage at which a first derivative of the source-drain current is zero.

22. The method of claim 21, wherein the step of identifying the singularity point comprises a coarse identification and a fine identification.

23. The method of claim 22, wherein the coarse identification is performed by adjusting the back gate voltage, and wherein the fine identification is performed by adjusting the working electrode voltage.

24. The method of claim 21, further comprising correcting for sensor drift based on the identified singularity point.

25. The method of claim 21, further comprising setting at least one of the back gate voltage, the working electrode voltage, or the source voltage to control a response to the analyte.

* * * * *